United States Patent [19]
Fitch et al.

[11] Patent Number: 5,397,798
[45] Date of Patent: Mar. 14, 1995

[54] BENZAMIDE AND SULFONAMIDE HYPOGLYCEMIC AGENTS

[75] Inventors: Lora L. Fitch; Klaus K. Schmiegel, both of Indianapolis, Ind.

[73] Assignee: Eli Lilly and Company, Indianpolis, Ind.

[21] Appl. No.: 918,191

[22] Filed: Jul. 21, 1992

Related U.S. Application Data

[63] Continuation of Ser. No. 629,510, Dec. 18, 1990, abandoned.

[51] Int. Cl.$^6$ .................. A61K 31/415; C07D 231/12
[52] U.S. Cl. ........................ 514/399; 514/400; 548/338.1
[58] Field of Search .................. 548/338.1; 514/399, 514/400

[56] References Cited

U.S. PATENT DOCUMENTS

| | | | |
|---|---|---|---|
| 3,497,529 | 2/1970 | Ott et al. | 549/77 |
| 4,113,871 | 9/1978 | Stach et al. | 424/272 |
| 4,221,815 | 9/1980 | Weyer et al. | 424/319 |
| 4,322,439 | 3/1982 | Klemm et al. | 424/319 |
| 4,351,770 | 9/1982 | Ogata et al. | 548/567 |
| 4,507,315 | 3/1985 | Ashton et al. | 514/396 |
| 4,703,055 | 10/1987 | Franceschini et al. | 548/342 |

FOREIGN PATENT DOCUMENTS

59482/86 7/1986 Australia .
2126225A 8/1982 United Kingdom .

OTHER PUBLICATIONS

Burger, Medicinal Chemistry 2d ed, Interscience 1960, pp. 72–86.
M. Tadayyon et al., *Diabetologia*, 30, 41 (1987).
Wright et al., J. Med Chem, 29, pp. 523–530, (1986).
Wright et al., J. Med Chem, 30, pp. 2277–2283, (1987).
Sohda et al., Chem. Pharmaceutical Bulletin, 30(10) pp. 3563–3573 (Oct., 1982).
Fujita et al., Diabetes, 32(9), pp. 804–810 (Sep., 1983).

*Primary Examiner*—Mary C. Lee
*Assistant Examiner*—Jacqueline Haley
*Attorney, Agent, or Firm*—Janet T. McClain

[57] ABSTRACT

The present invention provides novel benzamides and sulfonamides, formulations thereof, and intermediates thereto. The benzamides and sulfonamides of the present invention are useful as hypoglycemic agents and, accordingly, a method of using such compounds to lower a mammal's blood glucose level is also provided.

24 Claims, No Drawings

BENZAMIDE AND SULFONAMIDE HYPOGLYCEMIC AGENTS

This application is a continuation of application Ser. No. 07/629,510, filed Dec. 18, 1990, abandoned.

BACKGROUND OF THE INVENTION

Diabetes mellitus is a systemic disease characterized by disorders in the metabolism of insulin, carbohydrates, fats and proteins, and in the structure and function of blood vessels. The primary symptom of acute diabetes is hyperglycemia, often accompanied by glucosuria, the presence in urine of large amounts of glucose, and polyuria, the excretion of large volumes of urine. Additional symptoms arise in chronic or long standing diabetes. These symptoms include degeneration of the walls of blood vessels. Although many different organs are affected by these vascular changes, the eyes appear to be the most susceptible. As such, long-standing diabetes mellitus, even when treated with insulin, is a leading cause of blindness.

There are two recognized types of diabetes. Juvenile onset, or ketosis-prone, diabetes develops early in life with much more severe symptoms and has a near-certain prospect of later vascular involvement. Control of this type of diabetes is often difficult. The second type of diabetes is adult onset, or ketosis-resistant, diabetes which develops later in life, is milder and has a more gradual onset.

One of the most significant advancements in the history of medical science came in 1922 when Banting and Best demonstrated the therapeutic effects of insulin in diabetic humans. However, even today, a clear of the basic biochemical defects of the disease is not known, and diabetes is still a serious health problem. It is believed that two percent or more of the population of the United States is afflicted with some form of diabetes.

The introduction of orally effective hypoglycemic agents was an important development in the treatment of diabetes. Hypoglycemic agents are useful in the treatment of hyperglycemia by lowering blood glucose levels. Oral hypoglycemic agents are normally used in the treatment of adult onset diabetes.

A variety of biguanide and sulfonylurea derivatives have been used clinically as hypoglycemic agents. However, the biguanides tend to cause lactic acidosis and the sulfonylureas, though having good hypoglycemic activity, require great care during use because they frequently cause serious hypoglycemia.

In *Chemical & Pharmaceutical Bulletin*, 30, 3563 (1982), *Chemical & Pharmaceutical Bulletin*, 30, 3580 (1982) and *Chemical & Pharmaceutical Bulletin*, 32, 2267 (1984), reference is made to a variety of thiazolidinediones which have blood glucose and lipid lowering activities. Antidiabetic activity of ciglitazone was also reported in *Diabetes*, 32, 804 (1983). However, these compounds have proven difficult to use because of insufficient activities and/or serious toxicity problems.

The present invention relates to orally active hypoglycemic agents capable of lowering blood glucose levels in mammals. Accordingly, one object of the present invention is to provide compounds having excellent hypoglycemic activity. Another object of the present invention is to provide hypoglycemic compounds which exhibit minimal toxicity in the ethylmorphine N-demethylation toxicity test system, and which do not cause unfavorable side reactions such as lactic acidosis or serious hypoglycemia. It is believed that compounds capable of achieving the objects of the present invention may be useful for treating diabetes. Other objects, features and advantages of the present invention will become apparent from the subsequent description and the appended claims.

SUMMARY OF THE INVENTION

The present invention relates to a method for lowering blood glucose levels in mammals comprising administering an effective amount of a compound of formula I

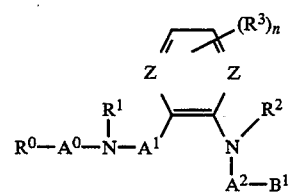

wherein:

$R^0$ is amino, $C_1$-$C_6$ alkylamino, $C_1$-$C_6$ dialkylamino or a heterocycle selected from the group consisting of

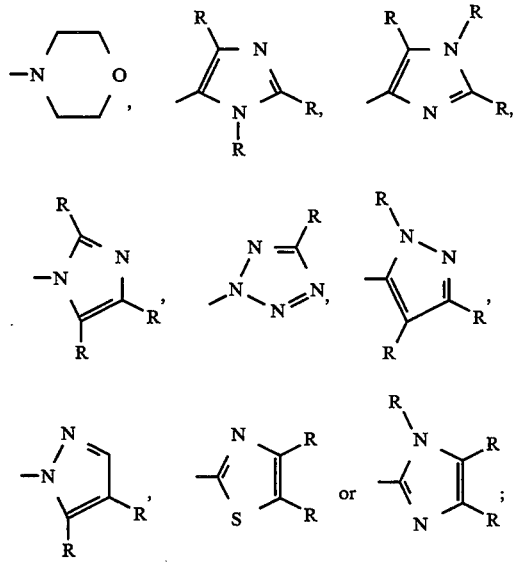

each R is independently hydrogen, $C_1$-$C_6$ alkyl or, if connected to a nitrogen atom, a protecting group;

$A^0$ is a divalent $C_1$-$C_6$ alkyl;

$R^1$ is hydrogen or $C_1$-$C_6$ alkyl;

$A^1$ is a carbonyl or sulfonyl moiety; both of Z are the same and are either —N— or —CH—;

$R^3$ is $C_1$-$C_4$ alkyl, halo, hydroxy, amino, trifluoromethyl, $C_1$-$C_4$ alkylamino, $C_1$-$C_4$ dialkylamino, nitro, cyano, carboxy, $C_1$-$C_4$ alkoxycarbonyl or $C_1$-$C_4$ alkoxy;

n is 0, 1, 2 or 3 when both of Z are —CH— and 0 when both of Z are —N—;

$R^2$ is hydrogen or $C_1$-$C_6$ alkyl;

$A^2$ is a carbonyl or sulfonyl moiety; and $B^1$ is

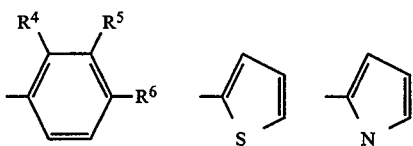 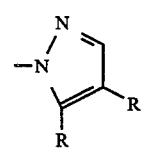

wherein $R^4$ is hydrogen, halo, $C_1$-$C_6$ alkyl, trifluoromethyl, phenyl, $C_1$-$C_4$ alkylphenyl, carboxy, $C_1$-$C_4$ alkoxycarbonyl, $C_1$-$C_4$ alkanoyl, hydroxy, mercapto, $C_1$-$C_6$ alkylthio, nitro, cyano, $C_1$-$C_6$ alkylsulfinyl or $C_1$-$C_6$ alkylsulfonyl; $R^5$ is hydrogen, 1,1-dimethylethyl or trifluoromethyl; and $R^6$ is hydrogen, halo, $C_1$-$C_6$ alkyl, trifluoromethyl, phenyl, $C_1$-$C_4$ alkylphenyl, carboxy, $C_1$-$C_4$ alkoxycarbonyl, $C_1$-$C_4$ alkanoyl, hydroxy, mercapto, $C_1$-$C_6$ alkylthio, nitro, cyano, $C_1$-$C_6$ alkylsulfinyl or $C_1$-$C_6$ alkylsulfonyl; with the provisos that:

i. at least one of $R^4$, $R^5$ and $R^6$ must be other than hydrogen;

ii. when $R^0$ is

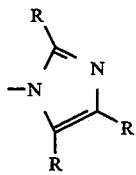

and both of Z are —CH— then $A^1$ must be a sulfonyl moiety;

iii. when $R^5$ is trifluoromethyl, $R^4$ and $R^6$ are hydrogen and $R^0$ is

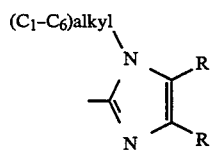

then $A^2$ must be a sulfonyl moiety;

iv. when $R^5$ is trifluoromethyl, $R^4$ and $R^6$ are hydrogen and $R^0$ is

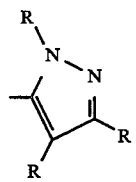

then at least one of $A^1$ or $A^2$ must be a sulfonyl moiety;

v. when $R^5$ is trifluoromethyl, $R^4$ and $R^6$ are hydrogen and $R^0$ is

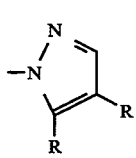

then at least one of $A^1$ or $A^2$ must be a sulfonyl moiety;

vi. when $R^6$ is halo, $R^4$ and $R^5$ are hydrogen and $R^0$ is

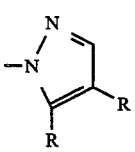

then $A^2$ must be a sulfonyl moiety;

vii. when both of Z are —N— and $R^0$ is

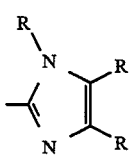

then $R^6$ must be other than halo;

viii. when $R^5$ is trifluoromethyl, $R^4$ and $R^6$ are hydrogen and $R^0$ is

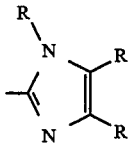

then $A^1$ must be a carbonyl moiety;

ix. when $R^6$ is fluoro, bromo or iodo, $R^4$ and $R^5$ are hydrogen and $R^0$ is

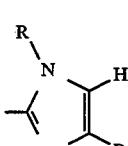

then $A^2$ must be a carbonyl moiety;

x. when $R^6$ is chloro, $R^4$ and $R^5$ are hydrogen and $R^0$ is

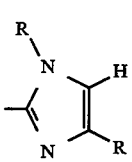

then $A^2$ must be a carbonyl moiety and $A^1$ must be a sulfonyl moiety;

xi. when $R^4$ and $R^5$ are hydrogen and $R^0$ is

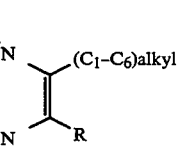

then $R^6$ must be other than chloro;

xii. when $R^6$ is halo, $R^4$ and $R^5$ are hydrogen and $R^0$ is

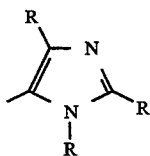

then at least one of $A^1$ or $A^2$ must be a sulfonyl moiety;

xiii. when $R^5$ is trifluoromethyl, $R^4$ and $R^6$ are hydrogen and $R^0$ is

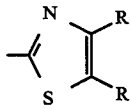

then $A^1$ must be a sulfonyl moiety; and xiv. when $B^1$ is

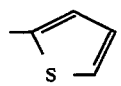

and both of Z are —CH— then at least one of $A^1$ or $A^2$ must be a sulfonyl moiety; or a pharmaceutically acceptable salt thereof, to a mammal in need of having its blood glucose level lowered.

The present invention also provides compounds of formula I, and the pharmaceutically acceptable salts thereof, wherein $A^0$, $R^1$, $A^1$, Z, $R^3$, n, $R^2$, $A^2$ and $B^1$ are as defined above, including the provisos, and $R^0$ may be any of the substituents shown above except

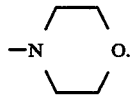

The present invention further provides pharmaceutical formulations comprising a compound of the present invention, or a pharmaceutically acceptable salt thereof, in combination with a pharmaceutically acceptable carrier, diluent or excipient therefor.

Finally, the present invention also provides compounds of formula II

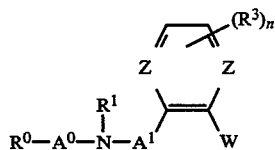

II wherein $R^0$, $A^0$, $R^1$, $A^1$, Z, $R^3$ and n are as defined for the compounds of the present invention, and W is —$NO_2$ or —$NHR^2$, where $R^2$ is hydrogen or $C_1$-$C_6$ alkyl, with the proviso that when $R^0$ is

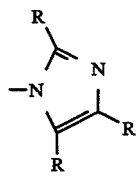

both of Z are —CH— then $A^1$ must be a sulfonyl moiety. Such compounds are useful as intermediates in preparing the compounds of formula I.

DETAILED DESCRIPTION OF THE INVENTION

All temperatures stated herein are in degrees Celsius. All units of measurement employed herein are in weight units except for liquids, which are in volume units.

As used herein, the term "$C_1$-$C_6$ alkyl" represents a straight or branched alkyl chain having from one to six carbon atoms. Typical $C_1$-$C_6$ alkyl groups include methyl, ethyl, n-propyl, isopropyl, n-butyl, sec-butyl, isobutyl, t-butyl, n-pentyl and the like. The term "$C_1$-$C_6$ alkyl" includes within its definition the term "$C_1$-$C_4$ alkyl".

"$C_1$-$C_6$ alkylamino" represents a straight or branched alkylamino chain having from one to six carbon atoms. Typical $C_1$-$C_6$ alkylamino groups include methylamino, ethylamino, n-propylamino and the like. The term "$C_1$-$C_6$ alkylamino" includes within its definition the term "$C_1$-$C_4$ alkylamino".

"$C_1$-$C_6$ dialkylamino" represents a straight or branched dialkylamino group having two alkyl chains of from one to six carbon atoms attached to a common nitrogen atom. Typical $C_1$-$C_6$ dialkylamino groups include dimethylamino, methylethylamino, methylisopropylamino, isopropyltert-butylamino, di-tert-butylamino, tert-butylhexylamino and the like. The term "$C_1$-$C_6$ dialkylamino" includes within its definition the term "$C_1$-$C_4$ dialkylamino".

"Divalent $C_1$-$C_6$ alkyl" represents a divalent, straight or branched alkyl chain having from one to six carbon atoms. Typical divalent $C_1$-$C_6$ alkyl chains include methylene, ethylene, n-propylene, isopropylene, n-butylene, isobutylene, tert-butylene, n-hexylene and the like.

"Halo" represents chloro, fluoro, bromo, or iodo.

"$C_1$-$C_4$ alkoxy" represents a straight or branched alkoxy chain having from one to four carbon atoms. Typical $C_1$-$C_4$ alkoxy groups include methoxy, ethoxy, n-propoxy, isopropoxy, n-butoxy, isobutoxy, tert-butoxy.

"$C_1$-$C_4$ alkoxycarbonyl" represents a straight or branched chain alkoxy group having from one to four carbon atoms attached to a carbonyl moiety. Typical $C_1$-$C_4$ alkoxycarbonyl groups include methoxycarbonyl, ethoxycarbonyl, n-propoxy-carbonyl, isopropoxycarbonyl, n-butoxycarbonyl, isobutoxycarbonyl and tert-butoxycarbonyl.

"$C_1$-$C_4$ alkylphenyl" represents a straight or branched chain alkyl group having from one to four carbon atoms attached to a phenyl ring. Typical $C_1$-$C_4$ alkylphenyl groups include methylphenyl, ethylphenyl, n-propylphenyl, isopropylphenyl, n-butylphenyl, isobutylphenyl and tert-butylphenyl.

"$C_1$-$C_4$ alkanoyl" represents a straight or branched chain alkyl group having from one to four carbon atoms attached to a carbonyl moiety. Typical $C_1$-$C_4$ alkanoyl groups include methanoyl, ethanoyl, n-propanoyl, isopropanoyl, n-butanoyl, isobutanoyl and tert-butanoyl.

"$C_1$-$C_6$ alkylthio" represents a straight or branched chain alkyl group having from one to six carbon atoms attached to a sulfur atom. Typical $C_1$-$C_6$ alkylthio groups include methylthio, ethylthio, n-propylthio, isopropylthio, n-butylthio, isobutylthio, n-hexylthio and the like.

"$C_1-C_6$ alkylsulfinyl" represents a straight or branched chain alkyl group having from one to six carbon atoms attached to a sulfinyl moiety. Typical $C_1-C_6$ alkylsulfinyl groups include methylsulfinyl, ethylsulfinyl, n-propylsulfinyl, isopropylsulfinyl, n-butylsulfinyl, tert-butylsulfinyl, n-hexylsulfinyl and the like.

"$C_1-C_6$ alkylsulfonyl" represents a straight or branched chain alkyl group having from one to six carbon atoms attached to a sulfonyl moiety. Typical $C_1-C_6$ alkylsulfonyl groups include methylsulfonyl, ethylsulfonyl, n-propylsulfonyl, isopropylsulfonyl, isobutylsulfonyl, tert-butylsulfonyl and the like.

The term "a protecting group" can be any group commonly used to protect a nitrogen atom in a heterocyclic ring containing such atom. Such groups are well known and are described by, for example, Sundberg et al., J.O.C., 38, 3324 (1973); "Advances in Organic Chemistry", Raphael et al., Vol. 3, Interscience, New York, N.Y. (1963); "Protective Groups in Organic Synthesis", Greene, Wiley-Interscience, New York, N.Y. (1981); and McOmie, *Protective Groups in Chemistry*, Plenum Press, New York (1973). Preferred protecting groups are trityl (triphenylmethyl) and tert-butoxycarbonyl.

The pharmaceutically acceptable salts of the compounds of formula I are also included within the scope of the compounds, methods and formulations of the present invention.

The term "pharmaceutically acceptable salt" as used herein, refers to salts of the compounds of the above formula which are substantially non-toxic to living organisms. Typical pharmaceutically acceptable salts include those salts prepared by reaction of the compounds of formula I with a pharmaceutically acceptable mineral or organic acid. Such salts are known as acid addition salts.

Examples of pharmaceutically acceptable mineral acids which may be used to prepare pharmaceutically acceptable acid addition salts include hydrochloric acid, phosphoric acid, sulfuric acid, hydrobromic acid, hydroiodic acid, phosphorous acid and the like. Examples of pharmaceutically acceptable organic acids which may be used to prepare pharmaceutically acceptable acid addition salts include aliphatic mono and di-carboxylic acids, oxalic acid, carbonic acid, citric acid, succinic acid, phenyl-substituted alkanoic acids, hydroxy alkanoic and alkandioic acids, aromatic acids, aliphatic and aromatic sulfonic acids and the like. Such pharmaceutically acceptable salts thus include hydrochloride, hydrobromide, nitrate, sulfate, pyrosulfate, bisulfate, sulfite, bisulfite, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate and the like. Preferred pharmaceutically acceptable acid addition salts include those formed with hydrochloric acid and oxalic acid.

Compounds of formula I which contain a carboxy group may be converted to a pharmaceutically acceptable salt by reaction with a pharmaceutically acceptable base. Typical examples of such pharmaceutically acceptable bases include ammonia, amines such as triethanolamine, triethylamine, ethylamine and the like, and compounds of the general formula $MOR^7$, where M represents an alkali metal atom, e.g. sodium or potassium, and $R^7$ represents hydrogen or $C_1-C_4$ alkyl.

Compounds of formula I may contain more than one basic salt-forming group (for example, the nitrogen atoms when both $R^1$ and $R^2$ are hydrogen) which, depending on the substitution pattern on the rest of the compound of formula I, may be sufficiently basic to form di- and tri-acid addition salts with the stronger non-toxic mineral and organic acids. Thus, di- and tri-acid addition salts of hydrochloric, hydrobromic and similar strong acids may be prepared with many of the compounds of the present invention. Such di- and tri-acid addition salts are considered to be part of the present invention.

It should be recognized that the particular anion forming a part of any salt of this invention is not of a critical nature, so long as the salt as a whole is pharmacologically acceptable and as long as the anionic moiety does not contribute undesired qualities to the salt as a whole.

While all combinations of variables listed in the above formulas provide compounds having the ability to lower blood glucose levels in mammals, certain of the above compounds are preferred for such use. For example, preferred compounds of formula I are those compounds wherein $R^0$, $A^0$, $R^1$, $A^1$, Z, $R^2$, $R^3$, n, $A^2$, $B^1$ and $R^5$ are as defined above; each R is independently hydrogen or methyl; $R^4$ is hydrogen or halo; and $R^6$ is hydrogen, halo or $C_1-C_6$ alkyl.

Of these preferred compounds, especially preferred are those compounds wherein $R^1$ and $R^2$ are hydrogen or methyl and $A^0$ is methylene, ethylene or n-propylene.

Of these especially preferred compounds, exceptionally preferred compounds are those compounds wherein both of Z are —CH— and $R^0$ is

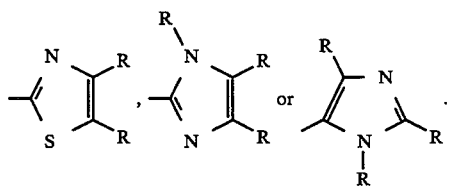

The most preferred compounds of the invention are
N-[2-[[[2-(1H-imidazol-2-yl)ethyl]amino]sulfonyl]-phenyl]-4-chlorobenzamide;

N-[2-(1H-imidazol-2-yl)ethyl]-2-[[4-(1,1-dimethylethyl)benzoyl]amino]benzamide;

N-[2-(1H-imidazol-2-yl)ethyl]-2-[[4-(1-methylethyl)-benzoyl]amino]benzamide;

N-[2-(1H-imidazol-2-yl)ethyl]-2-[[3-(trifluoromethyl)-benzoyl]amino]benzamide;

N-[2-(2-thiazolyl)ethyl]-2-[(4-chlorobenzoyl)amino]-benzamide;

N-[2-(1H-imidazol-2-yl)ethyl]-2-[[[3-(trifluoromethyl)-phenyl]sulfonyl]amino]benzamide;

N-[3-(1H-imidazol-2-yl)propyl]-2-[[4-(1,1-dimethylethyl)-benzoyl]amino ]benzamide;

N'-methyl-N-[2-(1H-imidazol-2-yl)ethyl]-2-[[3-(trifluoromethyl)benzoyl]amino ]benzamide; and the pharmaceutically acceptable salts thereof.

The following list of compounds is provided to further illustrate compounds of formula I included within the scope of the present invention.
N-[3-[5-(1,1-dimethylethyl)-1H-imidazol-4-yl]propyl]-2-[[[4-chlorophenyl]sulfonyl]amino]-5-hexyl-benzenesulfonamide N-[5-(1,2-dimethyl-1H-imidazol-4-yl)pentyl]-3-[[[4-(ethoxycarbonyl)phenyl]sulfonyl]amino]-2-pyrazinesulfonamide succinate N-[(1H-tetrazole-2-yl)methyl]-2-[[4-(methylsulfonyl)-benzoyl]methylamino]-3-nitro-benzamide N-methyl-N-[[[6-(5-methyl-1H-tetrazole-2-yl)hexyl]-3]][[4-phenylbenzoyl]amino-2-purazinesulfonamide N-[4-(1H-pyrazol-3-yl)butyl]-2-[[4-(isopropanoyl)-benzoyl]amino]-4-carboxybenzamide N-ethyl-N-[(1H-pyrazol-1-yl)methyl]-2-[[2-(methylmercapto) benzoyl]amino]-4-aminobenzamide N-[3-(1H-pyrazol-1-yl)propyl]-3-[[[4-propylthio)-phenyl]-sulfonyl]amino]-2-pyrazinesulfonamide N-[2-[[[5-(5-isopropyl-2-thiazolyl)pentyl]amino]sulfonyl] -5-carboxyphenyl]-2-fluoro-4-(trifluoromethyl)-benzamide phosphate N-[3-[4-(2-methylpropyl)-2-thiazolyl]propyl]-2-[[[3-(trifluoromethyl)phenyl]sulfonyl]amino]-4-propylaminobenzenesulfonamide N-[6-(methylamino)hexyl]-3-[[2-(n-butyl)benzoyl-]amino]-2-pyrazinesulfonamide methanesulfonate N-[2-[[[4-(1H-imidazol-2-yl)butyl]amino]sulfonyl]-5-hydroxyphenyl]-2-(trifluoromethyl)benzamide N-[3-(4-methyl-1H-imidazol-2-yl)propyl]-3-[[4-(nitro)-benzoyl]amino]-2-pyrazinecarboxamide N-[3-(1H-imidazol-1-yl)propyl]-3-[[4-(hydroxy)benzoyl]-amino]-2-pyrazinecarboxamide N-[2-[[[3-(2-methyl-1H-imidazol-1-yl)propyl]amino]sulfonyl]-4-cyanophenyl]-2,4-dichlorobenzamide N-[2-[[[6-(2-methyl-1H-imidazol-4-yl)hexyl]amino]-sulfonyl]-5-(1,1-dimethylethyl)phenyl]-4-cyanobenzamide The compounds of formula I can be prepared using chemical synthetic methods well known to one skilled in the art. A preferred procedure used to prepare such compounds involves reacting an appropriately substituted amine with an acid or sulfonyl halide moiety. This reaction may be represented by the following scheme:

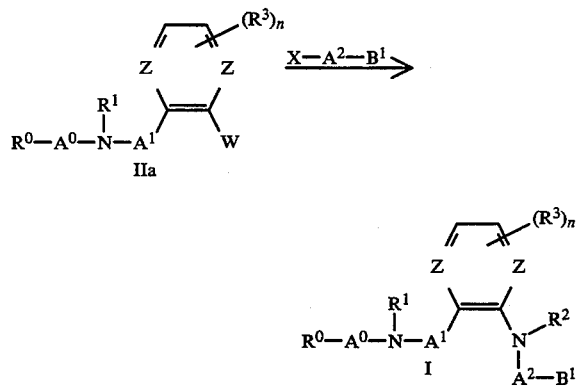

$R^0$, $A^0$, $R^1$, $A^1$, Z, $R^3$, n, $A^2$ and $B^1$ are as defined above, W is -$NHR^2$ (where $R^2$ is hydrogen or $C_1$-$C_6$ alkyl) and X is a halogen atom, preferably chlorine.

The above reaction is carried out by simply combining an appropriately substituted amine with a suitably substituted acid or sulfonyl halide moiety in a mutual inert solvent. The acid or sulfonyl halide substrate is generally employed in an amount ranging from about equimolar proportions to about a three molar excess of the acid or sulfonyl halide relative to the amine reactant. To ensure high product yields when using an amine substrate wherein $R^0$ is a heterocycle containing a secondary nitrogen atom, the acid or sulfonyl halide reactant should be employed in at least about a two molar excess relative to the amine reactant for reasons explained more fully below. Typical solvents suitable for use in this process include any standard organic solvent such as dichloromethane. Solvent choice is not critical so long as the solvent employed is inert to the ongoing reaction and the reactants are sufficiently solubilized to effect the desired reaction. A base, for example a trialkylamine such as triethylamine, pyridine, cyanomethane, potassium carbonate or the like, may, optionally, be added to promote the reaction by serving as an acid binding agent. An excess of the base may also serve as solvent for the reaction. The reaction is substantially complete after about 1 to 72 hours when conducted at a temperature in the range of from about 0° C. to the reflux temperature of the reaction mixture. The reaction is preferably conducted at a temperature in the range of from about 0° C. to about 30° C. for about 1 to 24 hours.

Once the reaction is complete, the product may be isolated by procedures well-known in the art, for example, the precipitated solid may be collected by filtration or the reaction solvent may be removed by extraction, evaporation or decantation. The product may be further purified, if desired, by common techniques such as crystallization or chromatography over solid supports such as silica gel or alumina.

In those amine substrates wherein $R^0$ is a heterocycle containing a secondary nitrogen atom, (i.e., a nitrogen atom substituted with a hydrogen atom), a second -$A^2$-$B^1$ substituent may attach itself to the $R^0$ nitrogen atom, thereby providing a bis-substituted compound. This second -$A^2$-$B^1$ substituent may be removed using standard organic chemistry techniques such as treating the bis-substituted compound with a $C_1$-$C_4$ alcohol, such as methanol, in combination with an alkali metal hydroxide such as sodium hydroxide (where $A^2$ is a sulfonyl moiety), or by heating the bis-substituted compound in a $C_1$-$C_4$ alcohol such as methanol (where $A^2$ is a carbonyl moiety).

A second procedure which may be used to prepare the compounds of formula I involves reacting a compound of formula III

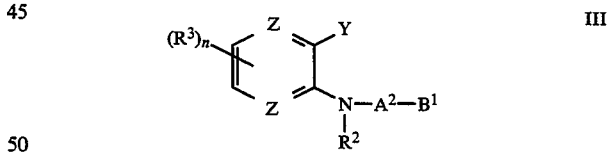

wherein:

$R^2$, $R^3$, $A^2$ and $B^1$ are as defined above;

both of Z are the same and are either —N— or —CH—;

n is 0 when both of Z are —N— and 0-3 when both of Z are —CH—; and

Y is —COOH, or a reactive derivative thereof such as an acid chloride or acid ester, or $SO_2X$ where X is halo, with an amine of formula IV

where $R^1$, $A^0$ and $R^0$ are as defined above. This reaction is also generally carried out in an inert organic solvent, such as dimethylformamide or dioxane, and preferably in the presence of an acid binding agent such as trialkylamine. Further, when Y is an acid chloride and $R^2$ is hydrogen, the amino portion of the compound of Formula III should first be protected using a standard amine protecting group or an acid salt of the amine in order to prevent the compound of Formula III from reacting with itself instead of the amine of Formula IV. The reaction is substantially complete after about 1 to 72 hours when conducted at a temperature in the range of from about 0° C. to the reflux temperature of the reaction mixture. Once the reaction is complete, the product may be isolated and purified using any of the techniques discussed above.

Yet a third method which may be used to prepare the compounds of Formula I entails reacting a compound of Formula III wherein $R^2$, $R^3$, $A^2$, $B^1$, Z and n are as set forth above and Y is —COOH with an amine of Formula IV as defined above in the presence of a dehydrating agent such as dicyclohexylcarbodiimide, N,N'-carbonyldiimidazole, phosphorus oxychloride and the like. This reaction is generally carried out in an inert organic solvent such as dimethylformamide or the like. The reaction is substantially complete after about 1 to 72 hours when conducted at a temperature in the range of from about 0° C. to the reflux temperature of the reaction mixture. Once the reaction is complete, of course, the product may be isolated using standard techniques.

Compounds of formula IIa

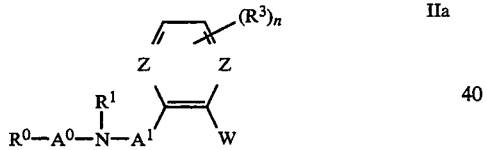

wherein $R^0$, $A^0$, $R^1$, $A^1$, Z, $R^3$, n and W are as defined above, are useful, as described above, for making the compounds of formula I. Compounds of formula IIa may be prepared by any one of four different methods as represented by the following reaction schemes:

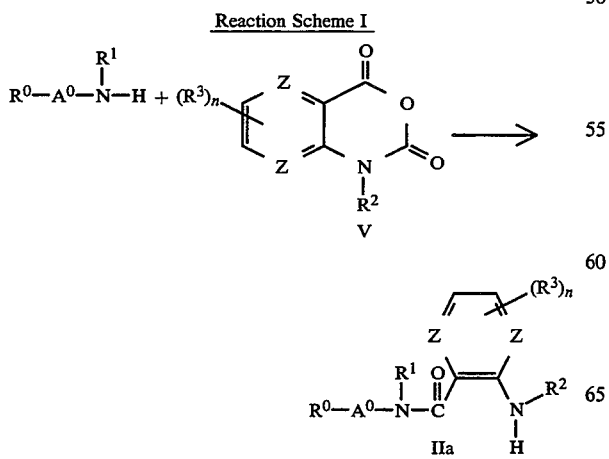

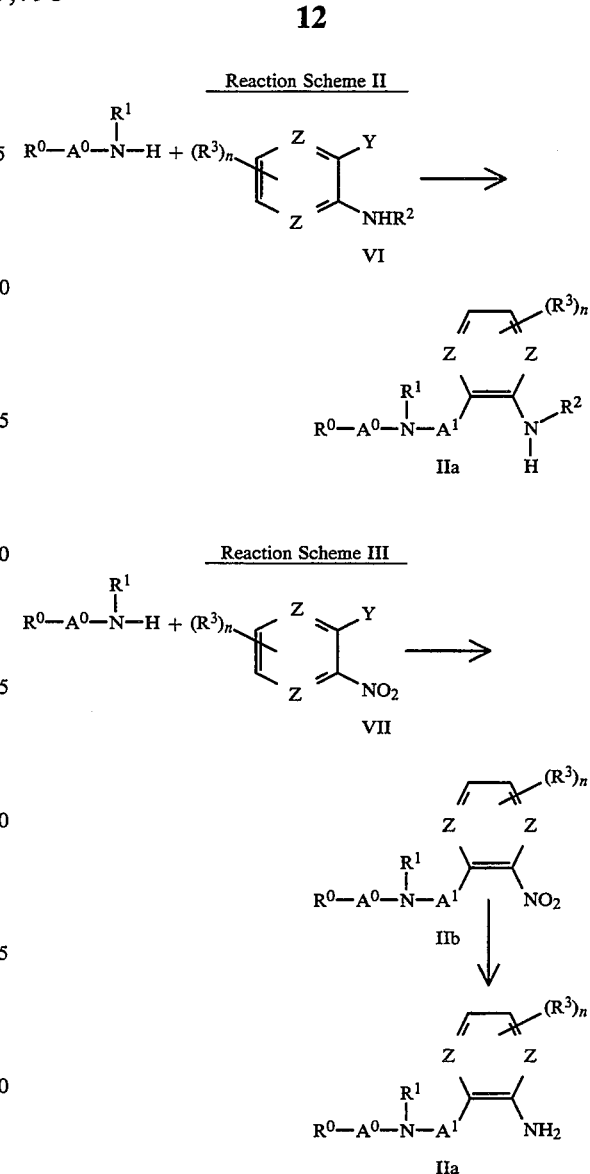

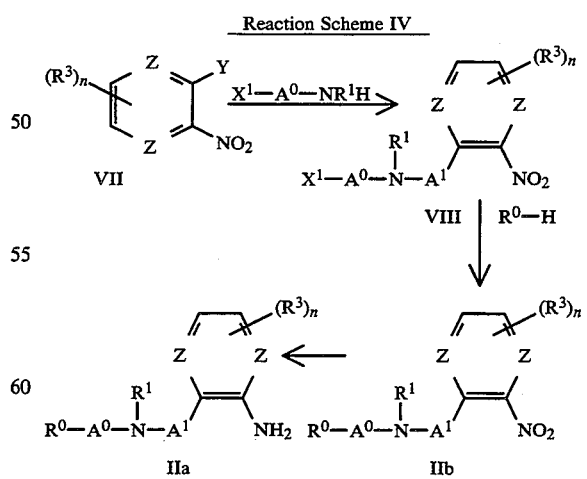

In Reaction Schemes I–IV, Z are both the same and are either —N— or —CH—; n is 0 when both of Z are —N— and 0–3 when both of Z are —CH—; and Y is —COOH, or a reactive derivative thereof, or -SO$_2$X where X is halo. In Reaction Scheme IV, $X^1$ is a halogen atom, preferably a bromine atom.

In Reaction Scheme I, above, compounds of formula IIa wherein $A^1$ is a carbonyl moiety may be prepared by reacting an appropriately substituted amine with approximately equimolar amounts of an anhydride of the formula V in a mutual inert solvent. Solvent choice is not critical so long as the reactants are sufficiently solubilized to effect the desired reaction and the solvent is inert to the reaction conditions employed. Preferred solvents are isopropanol and dioxane. The reaction is substantially complete after about 1 to 72 hours when conducted at a temperature in the range of from about 0° C. to the reflux temperature of the reaction mixture.

In Reaction Scheme II, above, compounds of formula IIa wherein $A^1$ is either a carbonyl or a sulfonyl moiety may be prepared by reacting an appropriately substituted amine with an appropriately substituted compound of formula VI. The reaction may be accomplished in a substantially similar manner as that described previously with respect to the reactions of a compound of formula III with a compound of formula IV.

In Reaction Scheme III, above, compounds of formula IIa wherein $A^1$ is either a carbonyl or a sulfonyl moiety may be prepared by reacting an appropriately substituted amine with an appropriately substituted compound of formula VII. The reaction may be accomplished in a substantially similar manner as that described with respect to Reaction Scheme II. However, since the compound of formula VII employed as a substrate in Reaction Scheme III has a nitro rather than an amino substituent, reduction of such substituent is required in order to provide the compounds of formula IIa. Reduction of the nitro substituent may be accomplished using any of the standard methods employed for reducing aromatic nitro compounds to their corresponding amines. Such methods include using a metal such as zinc, tin or iron and a strong acid such as hydrochloric acid; catalytic hydrogenation; using a sulfide such as ammonium sulfide or sodium hydrosulfide; using an aluminum hydride/aluminum chloride mixture; or using hydrazine in combination with a catalyst. Catalytic hydrogenation, preferably using a palladium on carbon catalyst with a $C_1$-$C_4$ alcoholic solvent, is a particularly preferred method of reduction.

Reaction Scheme IV, above, may be used to prepare compounds of formula IIa having an $R^0$ moiety which is amino, $C_1$-$C_6$ alkylamino, $C_1$-$C_6$ dialkylamino or a heterocycle containing a secondary nitrogen atom (i.e., a nitrogen atom substituted with a hydrogen atom). In Reaction Scheme IV, compounds of formula IIa may be prepared by reacting an amino substituted halide with an appropriately substituted compound of formula VII. The reaction may be accomplished substantially in the same manner as that described with respect to Reaction Scheme II. The halo substituted reaction product obtained (compound VIII) is then reacted with ammonia, a $C_1$-$C_6$ alkylamine, a $C_1$-$C_6$ dialkylamine or a heterocycle containing a secondary nitrogen atom, for example tetrazole, imidazole, morpholino, pyrazole or the like, in order to replace the halogen atom of compound VIII with the desired $R^0$ moiety. Depending on which of the above is reacted with the compound of formula VIII, different isomeric reaction products may be obtained (i.e., alkylation may occur at different nitrogen atoms on certain of the heterocyclic rings employed in Reaction Scheme IV). These isomers may be separated using standard purification techniques to provide the specific isomer desired. Again, since the compound of formula VII employed in Reaction Scheme IV has a nitro rather than an amino substituent, reduction of such nitro substituent is required in order to provide the amino compounds of formula IIa. Reduction of such nitro substituent may be accomplished using any of the methods discussed in Reaction Scheme III, above.

The compounds of formula I can be converted to their pharmaceutically acceptable salts by the application or adaptation of known methods. For example, compounds of formula I may be converted to their pharmaceutically acceptable acid addition salts by reacting the free base form of the compound of formula I with about one equivalent of an appropriate acid dissolved or suspended in a suitable solvent, followed, if necessary, by evaporation of all or part of the solvent and collection of the solid salt. Solvent choice is not critical so long as the reactants are sufficiently solubilized to effect the desired reaction. Typical solvents include acetone, methanol, ethanol, diethyl ether and the like.

Compounds of formula I may contain more than one basic salt-forming group (for example, the nitrogen atoms when both $R^1$ and $R^2$ are hydrogen) which, depending on the substitution pattern on the rest of the compound, may be sufficiently basic to form di- and tri-salts with stronger non-toxic acids. These compounds can be prepared using substantially the same procedure as that outlined above with respect to monosalts, using about two or three molar equivalents of the acid relative to the free base compound of formula I.

Compounds of formula I containing a carboxy group may be converted to their salts of pharmaceutically acceptable bases by reaction with an appropriate base, for example ammonia, an amine such as dimethylamine and the like, or a compound of the general formula $MOR^7$ where M represents an alkali metal such as sodium or potassium and $R^7$ represents a $C_1$-$C_4$ alkyl group or hydrogen, in a suitable solvent. Typical solvents which may be used include methanol, ethanol or a mixture of acetone and water. The salt may be recovered using techniques well-known to those skilled in the art.

It will be understood by those skilled in the art that in performing the processes described above it may be desirable to introduce chemical protecting groups into the reactants in order to prevent secondary reactions from taking place. For example, in the methods for preparing those compounds wherein $R^3$, $R^4$ and $R^6$ are hydroxy, such substituents may be converted into a benzyloxy group, or some other protected hydroxy group, before undergoing the reactions described above, with subsequent removal of the protecting group.

Furthermore, any amino, alkylamino and carboxy groups which may be present may be protected by any protecting group which is usually employed for protecting amines or carboxylic acids, and whose use does not adversely affect the remainder of the molecule's ability to react in the manner desired. For example, any amino and alkylamino groups can be protected by radicals such as tert-butoxycarbonyl, 2,2,2-trichloroethoxycarbonyl, trichloroacetyl, trityl, benzyl, dibenzyl, benzyloxycarbonyl, p-nitrobenzyloxycarbonyl, p-methoxybenzyloxycarbonyl, chloroacetyl, trifluoroacetyl and the like. Any carboxy groups can be protected by radicals such as methoxymethyl, tert-butyl, benzhydryl, p-nitrobenzyl or p-methoxybenzyl and the like. These various protective radicals can then be removed simultaneously or successively by methods well-known to those skilled in the art.

In addition, it may be desirable to change the nature of one or more of the substituents at an appropriate stage during the synthesis of the compounds of the invention. For example, the compounds of formula I wherein $R^3$ represents an amino group may be prepared from the corresponding compounds of formula I wherein $R^3$ is a nitro group using known methods for such reduction. Compounds of formula I wherein $R^3$ represents an amino group may be transformed to diazonium salts, which compounds are then useful in synthesizing compounds having other $R^3$ substituents, for example, an iodine atom.

The starting materials used to prepare the compounds of the present invention and the compounds employed in the method of the present invention are either commercially available or readily prepared by known processes.

The following Examples further illustrate specific aspects of the present invention. It is to be understood, however, that the Examples are included for illustrative purposes only and are not intended to limit the scope of the invention in any respect and should not be so construed.

EXAMPLE 1

N-[3-(1H-Imidazol-1-yl)propyl ]-2-[[[3-(trifluoromethyl) phenyl]sulfonyl]amino]benzenesulfonamide A. N-[(3-Imidazol-1-yl)propyl]-2-nitrobenzenesulfonamide A solution of 11.5 g (0.0519 mol) of o-nitrobenzenesulfonyl chloride in approximately 30 ml of dichloromethane was added slowly over several minutes to a cold (0° C.) solution of 5.4 g (0.043 mol) of N-(3-aminopropyl)imidazole in 100 ml pyridine, under nitrogen. The resulting reaction mixture was gradually warmed to room temperature and allowed to react overnight. When the reaction was complete, as determined by thin layer chromatography, the reaction solution was reduced to dryness under reduced pressure. The resultant oil was redissolved in an ethyl acetate/aqueous sodium bicarbonate mixture containing trace amounts of ethanol and propanone. The resulting layers were separated, the organic layer was washed with water and then reduced to dryness under reduced pressure to provide a gum. This gum was then purified using column chromatography (8000 ml of a gradient eluent of 0–10% methanol in dichloromethane). The fractions containing the desired product were combined, reduced to dryness under reduced pressure and then recrystallized from methanol to provide 3.4 g of the desired subtitled intermediate (m.p. 166°–170° C).

B. 2-Amino-N-[(3-imidazol-1-yl)propyl ]benzenesulfonamide

A suspension was prepared containing 3.4 g (0.011 mol) of the subtitled intermediate of Example 1A and 2.0 g of 5% palladium on carbon in 200 ml of a 3:1 methanol/ethanol solution. The suspension was shaken under 40 psi hydrogen for 1¼ hours. After that time, approximately 100 ml of ethanol were added and the 5% palladium on carbon was removed by filtration. The filtrate was reduced to dryness under reduced pressure to provide an oily solid which was recrystallized from an ethanol/diethyl ether solution to provide 1.96 g of the desired subtitled intermediate (m.p. 137°–141° ).

C. N-[3-(1H-Imidazol-1-yl)propyl ]-2-[[[3-(trifluoromethylphenyl]sulfonyl]amino]-benzenesulfonamide A solution of 1.93 g (0.00788 mol) of m-trifluoromethylbenzenesulfonyl chloride in 5 ml of dichloromethane was added dropwise to a cold (0° C.) solution of 1.92 g (0.00685 mol) of the subtitled intermediate of Example 1B in 40 ml of pyridine, under nitrogen. The resulting reaction mixture was gradually warmed to room temperature and allowed to react overnight. When the reaction was complete, as determined by thin layer chromatography, the reaction solution was reduced to dryness under reduced pressure. The resultant residue was redissolved in an ethyl acetate/aqueous sodium bicarbonate mixture. The resulting layers were separated and the organic layer was washed with water, then reduced to dryness under reduced pressure to provide a foam. This foam was purified using column chromatography (8000 ml of a gradient eluent of 0–25% methanol in a 1% ammonia in dichloromethane solution). The fractions containing the desired product were combined, reduced to dryness under reduced pressure and then recrystallized from an ethanol/water water solution to provide 1.4 g of the desired titled compound (m.p. 85°–88° C.).

Analysis on $C_{19}H_{19}F_3N_4O_4S_2$: Calc.: C, 46.72; H, 3.92; N, 11.47; Found: C, 46.54; H, 4.06; N, 11.16.

EXAMPLE 2

N-[2-[[[3-(1H-Imidazol-1-yl)propyl]amino]sulfonyl]-phenyl]-3-(trifluoromethyl)benzamide A solution of 4.24 g (0.0203 mol) of m-trifluoromethylbenzoyl chloride in 10 ml of dichloromethane was added dropwise to a solution of 4.35 g (0.0153 mol) of 2-amino-N-[(3-imidazol-1-yl)propyl]benzenesulfonamide, prepared as in Examples 1A and 1B, in 70 ml of pyridine, under nitrogen. When the reaction was complete, as determined by thin layer chromatography, the resulting reaction mixture was reduced to dryness under reduced pressure. The resultant oil was dissolved in an ethyl acetate/aqueous sodium bicarbonate mixture. The resulting layers were separated, the organic layer was washed with water and again reduced to dryness under reduced pressure to provide an oil. This oil was then purified using column chromatography (8000 ml of a gradient eluent of 0–15% methanol in chloroform). The fractions containing the desired product were combined, reduced to dryness under reduced pressure and then recrystallized from an ethanol/hexane/diethyl ether solution to provide 4.08 g of the desired titled compound (m.p. 145°–147° C.).

Analysis on $C_{21}H_{19}F_3N_4O_3S$: Calc.: C, 53.09; H, 4.23; N, 12.38; Found: C, 53.04; H, 4.16; N, 12.32.

EXAMPLE 3

N-[2-(1-Methyl-1H-imidazol-2-yl)ethyl]-2-[[[3-(trifluoromethyl)phenyl]sulfonyl]amino]benzenesulfonamide A. N-[2-(1-Methyl-1H-imidazol-2-yl)ethyl]-2-nitrobenzenesulfonamide The subtitled intermediate was prepared substantially in accordance with the method described in Example 1A using 9.8 g (0.0442 mol) of o-nitrobenzenesulfonyl chloride and 4.42 g (0.0353 mol) of 2-(2-aminoethyl)-1-methylimidazole. Following layer separation, the water layer was extracted several times with chloroform and the resultant extractions were combined and reduced to dryness under reduced pressure to provide a solid. This solid was redissolved in a methanol/ethanol mixture, containing a small amount of water and chloroform. The material which did not dissolve was removed by filtration, providing 1.84 g of the desired subtitled intermediate. The filtrate was cooled to about 0° C. and a diethyl ether/hexane solution was added to it. Solids precipitated and were recovered by filtration to provide 3.7 g of the desired subtitled intermediate (total recovery of the intermediate 5.54 g; m.p. 193°–199° C.).

Analysis for $C_{12}H_{14}N_4O_4S$: Calc.: C, 46.45; H, 4.55; N, 18.05; Found: C, 46.33: H, 4.58; N, 17.78.

B. 2-Amino-N-[2-(1-methyl-1H-imidazol-2-yl)ethyl]-benzenesulfonamide

The subtitled intermediate was prepared substantially in accordance with the method detailed in Example 1B using 5.41 g (0.0174 mol) of the subtitled intermediate of Example 3A and 0.51 g of 5% palladium on carbon in a 1:1 ethanol/methanol solution. After reduction to dryness under reduced pressure, the resultant residue was recrystallized from an ethyl acetate/diethyl ether solution to provide 4.34 g of the desired subtitled intermediate (m.p. 95°–98° C.).

Analysis for $C_{12}H_{16}N_4O_2S$: Calc.: C, 51.41; H, 5.75; N, 19.99; Found: C, 51.16; H, 5.78; N, 19.75.

C. N-[2-(1-Methyl-1H-imidazol-2-yl)ethyl]-2-[[[3-(trifluoromethyl)phenyl]sulfonyl]amino]-benzenesulfonamide The titled compound was prepared substantially in accordance with the method set forth in Example 1C using 2.02 g (0.0072 mol) of the subtitled intermediate of Example 3B and 2.52 g (0.0103 mol) of m-trifluoromethylbenzenesulfonyl chloride. The reaction product was purified by recrystallization from an ethyl acetate/diethyl ether solution followed by recrystallization from a methanol/ethanol/diethyl ether solution to provide 2.31 g of the desired titled compound (m.p. 171°–176° C.).

Analysis for $C_{19}H_{19}F_3N_4O_4S_2$: Calc.: C, 46.72; H, 3.92; N, 11.47; Found: C, 46.66; H, 4.00; N, 11.44.

EXAMPLE 4

N-[2-[[[2-(1H-Imidazol-2-yl)ethyl]amino]sulfonyl]phenyl]-4-chlorobenzamide monohydrochloride A. N-[2-(1H-Imidazol-2-yl) ethyl]-2-nitrobenzenesulfonamide A solution of 105 g (0.472 mol) of o-nitrobenzenesulfonyl chloride in 100 ml of dichloromethane was added slowly to a cold (0° C.) solution of 26.2 g (0.236 mol) of 2-(2-aminoethyl)imidazole in 300 ml of pyridine, under nitrogen. The reaction mixture was gradually warmed to room temperature and allowed to react overnight. When the reaction was complete, as determined by thin layer chromatography, the solution was reduced to dryness under reduced pressure. The resultant residue was dissolved in a water/methanol/5N sodium hydroxide solution and stirred for 3 hours. The solution was then acidified with concentrated hydrochloric acid and filtered to remove inorganic impurities. The methanol was removed under reduced pressure from the reaction mixture and the remaining solution was basicified by addition of aqueous sodium bicarbonate. The desired product was extracted from this solution with a solution consisting of ethyl acetate and a small amount of ethanol. The organic extract was washed with water, dried with anhydrous sodium sulfate and reduced to dryness under reduced pressure to provide an oil. This oil was then purified using standard purification techniques to provide 37.7 g of the desired subtitled intermediate.

2-Amino-N-[2-(1H-imidazol-2-yl)ethyl]benzenesulfonamide dihydrochloride

Reduction of the subtitled intermediate of Example 4A was achieved substantially in accordance with the method detailed in Example 1B using 15.7 g (0.0530 mol) of N-[2-(1H-imidazol-2-yl)ethyl]-2-nitro-benzenesulfonamide and 2.0 g of 5% palladium on carbon in 200 ml of ethanol, with the exception that after removing the ethanol under reduced pressure the resultant oil was dissolved in methanol containing hydrochloric acid and diethyl ether. This solution was reduced to dryness under reduced pressure to provide a foamy oil which was recrystallized from cyanomethane containing a small amount of methanol to provide 0.70 g of the desired subtitled intermediate (153°–159° C.).

Analysis for $C_{11}H_{14}N_4O_2S \cdot 2HCl$: Calc.: C, 38.95; H, 4.75; N, 16.52; Found: C, 39.36; H, 4.70; N, 16.75.

C. N-[2-[[[2-(1H-Imidazol-2-yl)ethyl]amino]sulfonyl]phenyl]-4-chlorobenzamide monohydrochloride The titled compound was prepared substantially in accordance with the method detailed in Example 1C using 3.30 g (0.0187 mol) of p-chlorobenzoyl chloride and 2.50 g (0.00939 mol) of the subtitled intermediate of Example 4B, with the exception that after removing ethyl acetate the resultant residue was dissolved in methanol containing hydrochloric acid and diethyl ether. The resulting solution was reduced to dryness under reduced pressure. The desired product was recrystallized from diethyl ether containing a small amount of ethanol to provide 0.43 g of the desired titled compound (m.p. 236°–242° C.).

Analysis for $C_{18}H_{17}ClN_4O_3S \cdot HCl$: Calc.: C, 49.10; H, 3.98; N, 12.72; Found: C, 48.84; H, 4.13; N, 12.42.

EXAMPLE 5

N-[2-(1-Methyl-1H-imidazol-2-yl)ethyl]-2-[[[3-(trifluoromethyl)phenyl]sulfonyl]amino]benzamide The titled compound was prepared substantially in accordance with the method set forth in Example 1C using 4.84 g (0.0198 mol) of 2-amino-N-[2-(1-methyl-1H-imidazol-2-yl)ethyl]benzamide (prepared in a similar manner as the compound in Example 6A) and 5.25 g (0.0215 mol) of m-trifluoromethylbenzenesulfonyl chloride. After reducing the organic layer to dryness, the resulting yellow solid was recrystallized from an ethyl acetate/diethyl ether solution to provide 7.8 g of the desired titled compound (m.p. 127°–129° C.)

Analysis on $C_{20}H_{19}F_3N_4O_3S$: Calc.: C, 53.09; H, 4.23; N, 12.38; Found: C, 53.32; H, 4.16; N, 12.33.

EXAMPLE 6

N-[2-(1H-Imidazol-2-yl)ethyl]-2-[[(4-methylphenyl)sulfonyl]amino]benzamide

A. 2-Amino-N-[2-(1H-imidazol-2-yl)ethyl]benzamide

Twenty grams (0.123 mol) of isatoic anhydride were slowly added to a cold (0° C.) solution of 13.5 g (0.122 mol) of 2-(2-aminoethyl)imidazole in 220 ml isopropanol, under nitrogen. The reaction mixture was gradually warmed to room temperature and allowed to react. When the reaction was complete, as indicated by thin layer chromatography, the solution was reduced to dryness under reduced pressure and the resultant residue was redissolved in an ethyl acetate/aqueous sodium bicarbonate mixture. The resulting layers were separated, the organic layer was washed with water and reduced to dryness to provide a solid. This solid was recrystallized from ethanol containing a small amount of hexane to provide 24.1 g of the desired subtitled intermediate (m.p. 180°–185° C.).

Analysis for $C_{12}H_{14}N_4O$: Calc.: C, 62.59; H, 6.13; N, 24.33; Found: C, 62.53; H, 6.09; N, 24.14.

B. N-[2-(1H-Imidazol-2-yl)ethyl]-2-[[(4-methylphenyl)sulfonyl]amino]benzamide

A solution of 3.31 g (0.01738 mol) of p-toluenesulfonyl chloride in 10 ml of dichloromethane was added slowly to a cold (0° C.) solution of 2.00 g (0.00869 mol) of the subtitled intermediate of Example 6A in 35 ml of pyridine, under nitrogen. The reaction mixture was gradually warmed to room temperature and allowed to react overnight. When the reaction was complete, as indicated by thin layer chromatography, the solution was reduced to dryness under reduced pressure and the resultant residue was redissolved in a methanol/5N sodium hydroxide solution. This solution was stirred at room temperature for 3 hours and then reduced to dryness under reduced pressure. The resulting residue was first acidified with 3N hydrochloric acid and then basicified with sodium bicarbonate. The desired product was extracted with ethyl acetate and the extract was washed with a saturated sodium chloride solution, dried with anhydrous sodium sulfate and then reduced to dryness under reduced pressure to provide a solid. This solid was recrystallized from ethyl acetate containing a small amount of methanol to provide 2.58 g of the desired titled compound (m.p. 173°–181° C.).

Analysis for $C_{19}H_{20}N_4O_3S$: Calc.: C, 59.36; H, 5.29; N, 14.57; Found: C, 59.09; H, 5.19; N, 14.34.

EXAMPLE 7

N-[2-(1H-Imidazol-2-yl)ethyl]-2-[(2-thienylsulfonyl)-amino]benzamide monohydrochloride The titled compound was prepared substantially in accordance with the method detailed in Example 6B using 1.50 g (0.00651 mol) of 2-amino-N-[2-(1H-imidazol-2-yl)ethyl]benzamide, prepared as in Example 6A, and 1.62 g (0.00847 mol) of 2-thiophenesulfonyl chloride, with the exception that after removing ethyl acetate, the resultant residue was dissolved in methanol containing hydrochloric acid and diethyl ether. The resulting solution was reduced to dryness under reduced pressure and the product was recrystallized from water and dried for approximately 8 hours at 100° C. under reduced pressure to provide 0.99 g of the desired titled compound (m.p. 210°–213° C.).

Analysis for $C_{16}H_{16}N_4O_2 \cdot HCl$: Calc.: C, 46.54; H, 4.15; N, 13.57; Found: C, 46.43; H, 4.31; N, 13.75.

EXAMPLE 8

N-[2-(1H-Imidazol-2-yl)ethyl]-2-[[[4-(1-methylethyl)-phenyl]sulfonyl]amino]benzamide The titled compound was prepared substantially in accordance with the method detailed in Example 6B using 1.50 g (0.00651 mol) of 2-amino-[2-(1H-imidazol-2-yl)ethyl]benzamide, prepared as in Example 6A, and 2.85 g (0.01302 mol) of 4-isopropylbenzenesulfonyl chloride, with the exception that the solid was recrystallized from a 1:4 ethanol/hexanes solution to provide 1.68 g of the desired titled compound (m.p. 210°–218° C.).

Analysis for $C_{21}H_{24}N_4O_3S$: Calc.: C, 61.15; H, 5.86; N, 13.58; Found: C, 60.89; H, 5.75; N, 13.32.

EXAMPLE 9

N-[2-(1H-Imidazol-2-yl)ethyl]-2-[[[3-(trifluoromethyl)-phenyl]sulfonyl]amino]benzamide monohydrochloride A. 2-Amino-N-[2-(1-(1,1 dimethylethoxycarbonyl)-imidazol-2-yl)ethyl]benzamide A solution of 2.20 g (0.0098 mol) of di-tert-butyldicarbonate in 15 ml of dimethylformamide was added slowly to a cold (5° C.) solution of 2.14 g (0.00929 mol) of 2-amino-N-[2-(1H-imidazol-2-yl)ethyl]benzamide, prepared as in Example 6A, in 40 ml of dimethylformamide, under nitrogen. The resulting solution was gradually warmed to room temperature and allowed to react overnight. When the reaction was complete, as determined by thin layer chromatography, the reaction solution was reduced to dryness under reduced pressure to provide 4.1 g of an impure oil.

N-[2-(1H-Imidazol-2-yl)ethyl]-2-[[[3-(trifluoromethyl)phenyl]sulfonyl]amino]benzamide monohydrochloride The titled compound was prepared substantially in accordance with the method detailed in Example 6B using the oil prepared in Example 9A and 2.27 g (0.00929 mol) of 3-trifluoromethylbenzenesulfonyl chloride with the exception that after removing the dichloromethane and pyridine, the resultant oil was dissolved in several milliliters of 3N hydrochloric acid and the resulting solution was heated to remove the protecting group. Crystals formed, which were recovered by filtration, washed with water and then purified by crystallization from an ethanol/diethyl ether solution (twice) followed by recrystallization from an ethanol/ethyl acetate solution to provide 2.37 g of the desired titled compound (m.p. 181°–185° C.).

Analysis for $C_{19}H_{17}F_3N_4O_3S \cdot HCl$: Calc.: C, 48.06; H, 3.82; N, 11.80; Found: C, 48.00; H, 3.76; N, 11.84.

EXAMPLE 10

N-[3-(1H-Imidazol-1-yl)propyl]-3-[[[3-(trifluoromethyl)-phenyl]sulfonyl]amino]-2-pyrazinecarboxamide dihydrochloride A. 3-Amino-N-[3-(1H-imidazol-1-yl)propyl]-2-pyrazine carboxamide A solution of 19.09 g (0.0776 mol) of 1,1'-carbonyldiimidazole in approximately 200 ml of dimethylformamide was added slowly to a cold (0° C.) solution of 15.78 g (0.1135 mol) of 3-aminopyrazine-2-carboxylic acid in 150 ml of dimethylformamide. The resulting solution was gradually warmed to 25° C. and stirred for about two hours. A solution of 14.75 g (0.118 mol) of N-(3-aminopropyl)imidazole in approximately 40 ml of dimethylformamide was added and the resulting solution was allowed to react for four hours. After four hours, the reaction solution was reduced to dryness under reduced pressure. The resultant semi-solid was suspended in diethyl ether and the portion which did not dissolve was recovered by filtration. The recovered solid was then suspended in diethyl ether containing a small amount of ethyl acetate and the resulting mixture was stirred for about 48 hours. After stirring for 48 hours, the undissolved solid was isolated by filtration. This solid was purified by filtration through silica gel using 4% methanol in dichloromethane. The resultant purified material was recrystallized from a 1:4 dichloromethane/diethyl ether solution to provide 24.4 g of the desired subtitled intermediate (m.p. 118°–120° C.).

Analysis for $C_{11}H_{14}N_6O$: Calc.: C, 53.65; H, 5.73; N, 34.13; Found: C, 53.48; H, 5.75; N, 34.18.

N-[3-(1H-Imidazol-1-yl)propyl]-3-[[[3-(trifluoromethyl)phenyl]sulfonyl]amino]-2-pyrazinecarboxamide dihydrochloride A solution of 3.9 g (0.016 mol) of m-trifluoromethylbenzenesulfonyl chloride in 5 ml of dichloromethane was added dropwise to a cold (0° C.) solution of 3.6 g (0.015 mol) of the subtitled intermediate of Example 10A in 50 ml of pyridine, under nitrogen. The resulting solution was gradually warmed to room temperature and allowed to react overnight. By the next morning a large amount of a solid had precipitated out of solution to provide a slurry. The liquid in this slurry was removed under reduced pressure and the resulting residue was dissolved in an ethyl acetate/aqueous sodium bicarbonate mixture. The resulting layers were separated and the aqueous layer was extracted with ethyl acetate. The extract was washed with a saturated sodium chloride solution, dried over anhydrous sodium sulfate and reduced to dryness under reduced pressure to provide an oily foam. This foam was purified using column chromatography (4000 ml of a gradient eluent of 0–10% methanol in a 1% ammonia in dichloromethane solution followed by 2000 ml of a 4:1 dichloromethane/methanol with 1% ammonia solution). The fractions containing the desired compound were combined and reduced to dryness under reduced pressure to provide a solid. This solid, after purification using standard crystallization/recrystallization procedures, was dissolved in methanol containing diethyl ether and hydrochloric acid and the resultant solution was reduced to dryness under reduced pressure to provide 0.64 g of the desired titled compound.

Analysis for $C_{18}H_{17}F_3N_6O_3S \cdot 2HCl$: Calc.: C, 41.00; H, 3.63; N, 15.94; Cl 13.45; Found: C, 41.06; H, 3.81; N, 15.71; Cl 13.62.

EXAMPLE 11

N-[2-(1H-Imidazol-2-yl)ethyl]-2-[[4-(1,1-dimethylethyl)-benzoyl]amino]benzamide

The titled compound was prepared substantially in accordance with the method detailed in Example 6B using 1.50 g (0.00651 mol) of 2-amino-N-[2-(1H-imidazol-2-yl)ethyl]benzamide, prepared as in Example 6A, and 2.61 g (0.01302 mol) of p-tert-butylbenzoyl chloride, with the exception that after reducing the initial reaction mixture to dryness, the resultant residue was dissolved in methanol and heated at reflux for 30 minutes. The methanol solution was then reduced to dryness under reduced pressure and the resultant residue was dissolved in an ethyl acetate/aqueous sodium bicarbonate mixture. The resulting layers were separated and the organic layer was washed with a saturated sodium chloride solution, dried with anhydrous sodium sulfate and reduced to dryness under reduced pressure to provide a yellow oil. This oil was purified by twice crystallizing the material from diethyl ether containing a small amount of ethyl acetate to provide 1.64 g of the desired titled compound (m.p. 127°–132° C.).

Analysis for $C_{23}H_{26}N_4O_2$: Calc.: C, 70.75; H, 6.71; N, 14.35; Found: C, 70.53; H, 6.49; N, 14.13.

EXAMPLE 12

N-[2-(1H-Imidazol-2-yl)ethyl]-2-[[4-(1,1-dimethylethyl)-benzoyl]amino]benzamide monohydrochloride The titled compound was prepared substantially in accordance with the method detailed in Example 11 using 18.4 g (0.0799 mol) of 2-amino-N-[2-(1H-imidazol-2-yl)-ethyl]benzamide, prepared as in Example 6A, and 32.07 g (0.1598 mol) of p-tert-butylbenzoyl chloride, with the exception that after removing methanol the resultant oil was crystallized from ethyl acetate to provide an oily solid. This solid was purified by filtration through silica gel using 7% methanol in dichloromethane. The filtrate was reduced to dryness under reduced pressure and the resultant residue was recrystallized from an ethyl acetate/methanol/diethyl ether solution containing hydrochloric acid to provide 21.9 g of the desired titled compound (m.p. 207°–211° C.).

Analysis for $C_{23}H_{26}N_4O_2 \cdot HCl$: Calc.: C, 64.71; H, 6.37; N, 13.12; Cl, 8.30; Found: C, 64.57; H, 6.32; N, 12.93; Cl, 8.11.

EXAMPLE 13

N-[2-(1H-Imidazol-2-yl)ethyl]-3-[[4-(1,1-dimethylethyl)-benzoyl]amino]-2-pyrazinecarboxamide monohydrochloride A. 3-Amino-N-[2-(1H-imidazol-2-yl)ethyl]-2-pyrazinecarboxamide The subtitled intermediate was prepared substantially in accordance with the method detailed in Example 10A using 22.7 g (0.14 mol) of 1,1'-carbonyldiimidazole, 19.2 g (0.138 mol) of 3-aminopyrazine-2-carboxylic acid and 15.1 g (0.136 mol) of 2-(2-aminoethyl)-imidazole with the exception that an oil was obtained after removing dimethylformamide. This oil was recrystallized from a 1:1 ethyl acetate/diethyl ether solution to provide a solid which was triturated with a 2:1 ethyl acetate/methanol solution and allowed to stand overnight. After standing overnight, any solid which remained was isolated by filtration and then suspended in water to provide a slurry. This slurry was filtered to provide a solid which was recrystallized from a 2:1:1 dichloromethane/methanol/diethyl ether solution to provide 23.1 g of the desired subtitled intermediate (m.p. 203.5°–208° C.).

Analysis for $C_{10}H_{12}N_6O$: Calc.: C, 51.72; H, 5.21; N, 36.19; Found: C, 51.56; H, 5.22; N, 35.95.

Be N-[2-(1H-Imidazol-2-yl)ethyl]-3-[[4-(1,1-dimethylethyl)benzoyl]amino]-2-pyrazinecarboxamide monohydrochloride A solution of 7.34 g (0.0366 mol) of p-tert-butylbenzoyl chloride in 7 ml of dichloromethane was added dropwise to a cold (0° C.) solution of 2.00 g (0.00861 mol) of the subtitled intermediate of Example 13A in 35 ml of pyridine, under nitrogen. The resulting reaction mixture was gradually warmed to room temperature. When the reaction was complete, as determined by thin layer chromatography, the reaction solution was reduced to dryness under reduced pressure and the resulting residue was dissolved in 100 ml of methanol and heated at reflux for 30 minutes. The methanol was removed under reduced pressure and the resultant residue was redissolved in an ethyl acetate/aqueous sodium bicarbonate mixture. The resultant layers were separated and the organic layer was washed with water and a saturated sodium chloride solution, dried with anhydrous sodium sulfate and reduced to dryness under reduced pressure to provide an oil. This oil was partially dissolved in diethyl ether and the resulting suspension was filtered to provide a gummy solid. This solid was dissolved in methanol containing hydrochloric acid and diethyl ether and the resultant solution was reduced to dryness under reduced pressure to provide a solid. This solid was triturated with cyanomethane and the remaining solid residue was isolated by filtration. This solid was purified using standard purification techniques to provide 1.20 g of the desired titled compound (m.p. 201°–204° C.).

Analysis for $C_{21}H_{24}N_6O_2 \cdot HCl$: Calc.: C, 58.81; H, 5.88; N, 19.59; Found: C, 57.87; H, 5.67; N, 19.13.

EXAMPLE 14

N-[2-(1H-Imidazol-2-yl)ethyl]-2-[[4-phenylbenzoyl]amino]-benzamide

The titled compound was prepared substantially in accordance with the method detailed in Example 11 using 1.50 g (0.00651 mol) of 2-amino-N-[2-(1H-imidazol-2-yl)ethyl]benzamide, prepared as in Example 6A, and 3.76 g (0.01738 mol) of p-phenylbenzoyl chloride, with the exception that after removing ethyl acetate the final product was recrystallized from an ethyl acetate/methanol solution to provide 1.74 g of the desired titled compound (m.p. 197°–201° C.).

Analysis for $C_{25}H_{24}N_4O_2$: Calc.: C, 73.15; H, 5.40; N, 13.65; Found: C, 72.89; H, 5.19; N, 13.42.

EXAMPLE 15

N-[2-(1H-Imidazol-2-yl)ethyl]-2-[[3-(trifluoromethyl)-benzoyl]amino]benzamide monohydrochloride The titled compound was prepared substantially in accordance with the method detailed in Example 11 using 14.1 g (0.0612 mol) of 2-amino-N-[2-(1H-imidazol-2-yl)-ethyl]benzamide, prepared as in Example 6A, and 25.5 g (0.1224 mol) of m-trifluoromethylbenzoyl chloride with the exception that after removing ethyl acetate the resulting solid was suspended in methanol. To this suspension was added a diethyl ether/hydrochloric acid solution. The resulting solution was reduced to dryness under reduced pressure and the final product was recrystallized from an ethanol/diethyl ether solution to provide 22.97 g of the desired titled compound (m.p. 199°–201.5° C.).

Analysis for $C_{20}H_{17}N_4O_2 \cdot HCl$: Calc.: C, 54.74; H, 4.13; N, 12.76; Found: C, 54.47; H, 4.31; N, 12.82.

EXAMPLE 16

N-[2-(1H-Imidazol-2-yl)ethyl]-2-[[4-(1-methylethyl)-benzoyl]amino]benzamide monohydrochloride The titled compound was prepared substantially in accordance with the method detailed in Example 11 using 2.50 g (0.0109 mol) of 2-amino-N-[2-(1H-imidazol-2-yl)-ethyl]benzamide, prepared as in Example 6A, and 4.0 g (0.0217 mol) of p-isopropylbenzoyl chloride with the exception that, after removing ethyl acetate the resulting solid was purified using column chromatography (8000 ml of a gradient eluent of 0–15% methanol in a 1% ammonia in dichloromethane solution). The fractions containing the desired product were combined and reduced to dryness under reduced pressure to provide 2.1 g of a solid. This solid was then dissolved in methanol containing diethyl ether and hydrochloric acid and the resulting solution was again reduced to dryness under reduced pressure. The final product was recrystallized from an ethanol/diethyl ether solution to provide 2.37 g of the desired titled compound (m.p. 188°–192° C.).

Analysis for $C_{20}H_{17}N_4O_2 \cdot HCl$: Calc.: C, 63.99; H, 6.10; N, 13.57; Found: C, 63.74; H, 5.93; N, 13.35.

EXAMPLE 17

N-[2-(1H-Imidazol-2-yl)ethyl]-2-[[4-fluorobenzoyl]amino]-benzamide monohydrochloride The titled compound was prepared substantially in accordance with the method detailed in Example 11 using 2.00 g (0.00869 mol) of 2-amino-N-[2-(1H-imidazol-2-yl)-ethyl]benzamide, prepared as in Example 6A, and 2.81 g 0.01738 mol) of p-fluorobenzoyl chloride with the exception that separation of the aqueous and organic layers provided an aqueous slurry containing the desired product. This slurry was filtered and the solid obtained thereby was washed with ethyl acetate to provide 1.17 g of a solid. The filtrate was then reduced to dryness under reduced pressure to provide an additional 2.0 g of a solid. The solids were combined and then dissolved in methanol containing diethyl ether and hydrochloric acid and the resulting solution was reduced to dryness under reduced pressure. The final product was purified by crystallization from a cyanomethane/methanol solution followed by recrystallization from an ethanol/diethyl ether solution to provide 2.75 g of the desired titled compound (m.p. 209°–210° C.). Analysis for $C_{19}H_{17}FN_4O_2 \cdot HCl$: Calc.: C, 58.69; H, 4.67; N, 14.41; Found: C, 58.60; H, 4.80; N, 14.18.

EXAMPLE 18

N-[2-(1H-Imidazol-2-yl)ethyl]-2-[[4-acetylbenzoyl]amino]-benzamide oxalate

The titled compound was prepared substantially in accordance with the method detailed in Example 11 using 1.50 g (0.00651 mol) of 2-amino-N-[2-(1H-imidazol-2-yl)-ethyl]benzamide, prepared as in Example 6A, and 2.38 g (0.01302 mol) of p-acetylbenzoyl chloride with the exception that removal of ethyl acetate provided 3.3 g of a solid. This solid was dissolved in methanol and reacted with 0.311 (0.00651 mol) of oxalic acid. The resulting solution was reduced to dryness under reduced pressure to provide a solid. This solid was triturated in a methanol/propanone solution and filtered to provide 1.01 g of the desired titled compound (m.p. 168°–179° C.).

Analysis for $C_{21}H_{20}N_4O_3 \cdot C_2H_2O_4$: Calc.: C, 59.22; H, 4.75; N, 12.01; Found: C, 59.07; H, 4.65; N, 11.83.

EXAMPLE 19

N-[2-(1H-Imidazol-2-yl)ethyl]-2-[[(1H-pyrrol-2-yl)-carbonyl]amino]benzamide monohydrochloride The titled compound was prepared substantially in accordance with the method detailed in Example 11 using 1.50 g (0.00651 mol) of 2-amino-N-[2-(1H-imidazol-2-yl)-ethyl]benzamide, prepared as in Example 6A, and 1.36 g (0.0105 mol) of pyrrole-2-carboxylic acid chloride with the exception that after reducing the initial reaction solution to dryness the resultant residue was dissolved in methanol. The resulting solution was refluxed for approximately an hour and then reduced to dryness under reduced pressure to provide a solid. This solid was dissolved in an ethyl acetate/aqueous sodium bicarbonate mixture containing a small amount of ethanol. The resultant layers were separated and the organic layer was washed with a saturated sodium chloride solution, with anhydrous sodium sulfate and then reduced to dryness under reduced pressure. The resultant solid was dissolved in methanol containing diethyl ether and hydrochloric acid. After removing the methanol under reduced pressure, the final product was purified by crystallization from an ethanol/ethyl acetate solution, followed by recrystallization from a methanol/ethyl acetate solution, to provide 1.66 g of the desired titled compound (m.p. 237°–239° C.).

Analysis for $C_{17}H_{17}N_5O_2 \cdot HCl$: Calc.: C, 56.75; H, 5.04; N, 19.46; Found: C, 56.51; H, 5.04; N, 19.38.

EXAMPLE 20

N-[2-(1H-Imidazol-2-yl)ethyl]-2-[[4-(trifluoromethyl)-benzoyl]amino]benzamide

The titled compound was prepared substantially in accordance with the method detailed in Example 11 using 2.00 g (0.00869 mol) of 2-amino-N-[2-(1H-imidazol-2-yl)-ethyl]benzamide, prepared as in Example 6A, and 3.62 g (0.01738 mol) of p-trifluoromethylbenzoyl chloride with the exception that removal of ethyl acetate provided a solid. This solid was recrystallized from ethyl acetate containing a small amount of methanol to provide 3.00 g of the desired titled compound (m.p. 207°–215° C.).

Analysis for $C_{20}H_{17}F_3N_4O_2$: Calc.: C, 59.70; H, 4.26; N, 13.92; Found: C, 59.58; H, 4.25; N, 13.85.

EXAMPLE 21

N-[2-(1H-Imidazol-2-yl)ethyl]-2-[(2,4-dichlorobenzoyl)-amino]benzamide

The titled compound was prepared substantially in accordance with the method detailed in Example 11 using 2.00 g (0.00869 mol) of 2-amino-N-[2-(1H-imidazol-2-yl)-ethyl]benzamide, prepared as in example 6A, and 3.62 g (0.01738 mol) of p-trifluoromethylbenzoyl chloride with the exception that after removing ethyl acetate the final product was recrystallized from an ethyl acetate/hexane solution containing a small amount of methanol to provide 3.16 g of the desired titled compound (m.p. 178°–186° C.).

Analysis for $C_{19}H_{16}Cl_2N_4O_2$: Calc.: C, 56.59; H, 3.99; N, 13.89; Found: C, 56.39; H, 3.80; N, 13.65.

EXAMPLE 22

N-[2-(1H-Imidazol-2-yl)ethyl]-2-[[4-methylbenzoyl]amino]-benzamide

The titled compound was prepared substantially in accordance with the method detailed in Example 11 using 2.00 g (0.00869 mol) of 2-amino-N-[2-(1H-imidazol-2-yl)-ethyl]benzamide, prepared as in Example 6A, and 2.74 g (0.01738 mol) of p-toluoyl chloride with the exception that after removing ethyl acetate the resultant solid was purified by crystallization from an ethyl acetate/hexane solution containing a small amount of methanol, followed by recrystallization from an ethyl acetate/methanol solution, to provide 2.17 g of the desired titled compound (m.p. 209°–214° C.).

Analysis for $C_{20}H_{20}N_4O_2$: Calc.: C, 68.95; H, 5.79; N, 16.08; Found: C, 68.72; H, 5.76; N, 15.87.

EXAMPLE 23

N-[2-(1H-Pyrazol-3-yl)ethyl]-2-[[[3-(trifluoromethyl)-phenyl]sulfonyl]amino]benzamide monohydrochloride A. 2-Amino-N-[2-(1H-pyrazol-3-yl)ethyl]benzamide A slurry containing 17.7 g (0.109 mol) of isatoic anhydride in 80 ml of dioxane was slowly added to a cold (0° C.) solution of 12.1 g (0.109 mol) of 3-(2-aminoethyl)pyrazole in 150 ml of dioxane, under nitrogen. The reaction solution was gradually warmed to room temperature and allowed to react overnight. When the reaction was complete, as indicated by thin layer chromatography, water was added and the solution was reduced to dryness under reduced pressure. The resultant residue was dissolved in an ethyl acetate/aqueous sodium bicarbonate mixture. The resulting layers were separated and the organic layer was washed with water and reduced to dryness to provide an oil. This oil was purified by crystallization from dichloromethane, followed by recrystallization from an ethyl acetate/diethyl ether solution, to provide 12.8 g of the desired subtitled intermediate (m.p. 97°–99° C.).

Analysis for $C_{12}H_{14}N_4O$: Calc.: C, 62.59; H, 6.13; N, 24.33; Found: C, 62.45; H, 6.14; N, 24.11.

B. N-[2-(1H-Pyrazol-3-yl)ethyl]-2-[[[3-(trifluoromethyl)phenyl]sulfonyl]amino]benzamide monohydrochloride The titled compound was prepared substantially in accordance with the method detailed in Example 16 using 2.50 g (0.0109 mol) of the subtitled intermediate of Example 23A and 4.27 g (0.0174 mol) of m-trifluoromethylbenzenesulfonyl chloride to provide 0.76 g of the desired titled compound (m.p. 114°–117° C.).

Analysis for $C_{19}H_{17}N_4O_3S \cdot HCl$: Calc.: C, 48.06; H, 3.82; N, 11.80; Found: C, 47.78; H, 3.98; N, 11.74.

EXAMPLE 24

N-[2-[[[3-(1H-Pyrazol-1-yl)propyl]amino]sulfonyl]-phenyl]-3-(trifluoromethyl)benzamide A. N-[3-(1H-Pyrazol-1-yl)propyl]-2-nitrobenzenesulfonamide A solution of 11.97 g (0.0519 mol) of o-nitrobenzenesulfonyl chloride in 90 ml of cyanomethane was added slowly over several minutes to a cold (7° C.) solution of 10.7 g (0.0540 mol) of N-(3-aminopropyl)-pyrazole in a 3:1 cyanomethane/water solution containing 16.6 g (0.12 mol) of potassium carbonate, under nitrogen. The resulting reaction solution was warmed to room temperature and allowed to react. When the reaction was complete, as determined by thin layer chromatography, the reaction solution was poured into approximately 450 ml of ethyl acetate. The resulting aqueous and organic layers were separated and the organic layer was washed with both an aqueous potassium carbonate solution and an aqueous sodium chloride solution and then reduced to dryness under reduced pressure to provide an oil. This oil was purified using column chromatography (8000 ml of a gradient eluent of from 0 to 5% methanol in methylene chloride). The fractions containing the desired product were combined, reduced to dryness under reduced pressure and then recrystallized from a 1:2 ethyl acetate/diethyl ether solution to provide 13.97 g of the desired subtitled intermediate (m.p. 105°109° C.).

Analysis for $C_{12}H_{14}N_4O_4S$: Calc.: C, 46.44; H, 4.55; N, 18.05; Found: C, 46.73; H, 4.74; N, 18.26.

B. 2-Amino-N-[3-(1H-pyrazol-1-yl)propyl]benzenesulfonamide

The subtitled intermediate was prepared substantially in accordance with the method detailed in Example 1B using 13.45 g (0.0433 mol) of the subtitled intermediate of Example 24A and 2.0 g of 5% palladium on carbon in a 2:1 ethanol/methanol mixture to provide 12.39 g of the desired subtitled intermediate.

Analysis for $C_{12}H_{16}N_4O_2S$: Calc.: C, 51.41; H, 5.75; N, 19.98; Found: C, 51.20; H, 5.79; N, 19.76.

C. N-[2-[[[3-(1H-Pyrazol-1-yl)propyl]amino]-sulfonyl]phenyl]-3-(trifluoromethyl)-benzamide The titled compound was prepared substantially in accordance with the method detailed in Example 2 using 3.1 g (0.011 mol) of the subtitled intermediate of Example 24B and 2.65 g (0.013 mol) of m-trifluoromethylbenzoyl-benzoyl chloride with the exception that the final product was purified by crystallization from an ethyl acetate/hexane solution to provide 3.91 g of the desired titled compound (m.p. 108°–111° C.).

Analysis for $C_{20}H_{19}F_3N_4O_3S$: Calc.: C, 53.07; H, 4.23; N, 12.38; Found: C, 53.29; H, 4.36; N, 12.58.

EXAMPLE 25

N-[3-(1H-Pyrazol-1-yl)propyl]-2-[[[3-(trifluoromethyl)phenyl]amino]benzamide monohydrochloride A. N-[3-(1H-Pyrazol-1-yl)propyl]-2-nitrobenzamide The subtitled compound was prepared substantially in accordance with the method detailed in Example 24A using 6.0 g (0.030 mol) of N-(3-aminopropyl)-pyrazole, 8.5 g of potassium carbonate and 2.65 g (0.013 mol) of o-nitrobenzoyl chloride with the exception that the final product was purified by crystallization from a cyanomethane/diethyl ether solution, followed by recrystallization from an ethanol/diethyl ether solution, to provide 6.62 g of the desired subtitled intermediate (m.p. 78°–81° C.).

B. 2-Amino-N-[3-(1H-pyrazol-1-yl)propyl]benzamide

The subtitled compound was prepared substantially in accordance with the method detailed in Example 1B using 6.79 g (0.0248 mol) of the subtitled intermediate of Example 25A and 0.55 g of 5% palladium on carbon in ethanol with the exception that the product was recrystallized from toluene to provide 5.76 g of the desired subtitled intermediate (m.p. 96.5°–102.5° C.).

Analysis for $C_{13}H_{16}N_4O$: Calc.: C, 63.91; H, 6.60; N, 22.93; Found: C, 63.71; H, 6.45; N, 23.21.

C. N-[3-(1H-Pyrazol-1-yl)propyl]-2-[[[3-(trifluoromethyl)phenyl]sulfonyl]amino]benzamide monohydrochloride The titled compound was prepared substantially in accordance with the method detailed in Example 1C using 5.66 g (0.0233 mol) of the subtitled intermediate of Example 25B in 100 ml of dichloromethane and 6.5 ml (0.0464 mol) of triethylamine and 8.08 g (0.033 mol) of m-trifluoromethylbenzenesulfonyl chloride in 10 ml of dichloromethane. The product was purified using column chromatography (2500 ml dichloromethane; 1950 ml 2% methanol in dichloromethane, isocratic eluent). The fractions containing the desired product were combined and reduced to dryness under reduced pressure to provide 8.1 g of an oil. This oil was dissolved in methanol containing diethyl ether and hydrochloric acid and the resulting solution was reduced to dryness under reduced pressure. The final product was recrystallized from an ethyl acetate/diethyl ether solution to provide 3.10 g of the desired titled compound (m.p. 138°–146° C.).

Analysis for $C_{20}H_{19}F_3N_4O_3S\cdot HCl$: Calc.: C, 49.13; H, 4.12; N, 11.46; Found: C, 49.41; H, 4.32; N, 11.35.

EXAMPLE 26

N-[3-(1H-Pyrazol-1-yl)propyl]-2-[[[3-(trifluoromethyl)phenyl]phenyl]sulfonyl]amino]benzenesulfonamide The titled compound was prepared substantially in accordance with the method detailed in Example 1C using 3.0 g (0.011 mol) of the subtitled intermediate of Example 24B and 3.01 g (0.012 mol) of m-trifluoromethylbenzenesulfonyl chloride with the exception that the final product was recrystallized from an ethyl acetate/hexane solution to provide 1.65 g of the desired titled compound (m.p. 85°–87° C.).

Analysis for $C_{19}H_{19}F_3N_4O_4S_2$: Calc.: C, 46.71; H, 3.92; N, 11.47; Found: C, 46.99; H, 3.93; N, 11.47.

EXAMPLE 27

N-[3-(2H-Tetrazol-2-yl)propyl]-2-[[[3-(trifluoromethyl)-phenyl]sulfonyl]amino]benzamide A. N-[3-(1H-Tetrazol-2-yl)propyl]-2-nitrobenzamide A solution of 24.5 g (0.085 mol) of N-(3-bromopropyl)-2-nitrobenzamide in 75 ml of dimethylformamide was slowly added to a solution of 7.00 g (0.10 mol) of tetrazole. The resulting solution was heated to 50° C. and allowed to react overnight. When the reaction was complete, as determined by thin layer chromatography, most of the dimethylformamide was removed under reduced pressure. The resultant residue was diluted with water, causing a precipitate to form. The precipitate was isolated by filtration and dried under vacuum. Thin layer chromatography and nuclear magnetic resonance spectroscopy indicated the presence of two isomers; namely, the N-1 and N-2 alkylated tetrazoles (75:25 ). The N-2 alkylated compound was isolated by column chromatography to provide 4.3 g of the desired subtitled intermediate. The N-1 alkylated compound was isolated by twice crystallizing the precipitate from cyanomethane to provide 3.72 g of that compound. (m.p. 148°–150° C.).

Analysis for $C_{11}H_{12}N_6O_2$: Calc.: C, 47.83; H, 4.38; N, 30.42; Found: C, 48.01; H, 4.43; N, 30.27.

B. 2-Amino-N-[3-(2H-tetrazol-2-yl)propyl]benzamide

The subtitled intermediate was prepared substantially in accordance with the method detailed in Example 1B using 4.2 g (0.015 mol) of the subtitled intermediate of Example 27A and 2.0 g of 5% palladium on carbon in ethanol. After the filtrate was reduced to dryness under reduced pressure the residue obtained thereby was recrystallized from diethyl ether to provide 3.2 g of the desired subtitled intermediate (m.p. 60°–61.5° C.).

Analysis for $C_{11}H_{14}N_6O$: Calc.: C, 53.65; H, 5.73; N, 34.12; Found: C, 53.39; H, 5.59; N, 33.95.

C. N-[3-(2H-Tetrazol-2-yl)propyl]-2-[[[3-(trifluoromethyl)phenyl]sulfonyl]amino]-benzamide The titled compound was prepared substantially in accordance with the method detailed in Example 1C using 2.43 g (0.00988 mol) of the subtitled intermediate of Example 27B and 2.60 g (0.011 mol) of m-trifluoromethylbenzenesulfonyl chloride with the exception that the final product was purified using column chromatography. The fractions containing the desired product were combined, reduced to dryness under reduced pressure, recrystallized from diethyl ether and then dried under vacuum at 45° C. overnight to provide 3.69 g of the desired titled compound (m.p. 67°–69° C.).

Analysis for $C_{19}H_{19}F_3N_4O_4S_2$: Calc.: C, 47.58; H, 3.77; N, 18.49; Found: C, 47.64; H, 3.79; N, 18.33.

EXAMPLE 28

N-[2-(1H-Imidazol-4-yl)ethyl]-2-[[3-(trifluoromethyl)-benzoyl]amino]benzamide

A. 2-Amino-N-[2-(1H-imidazol-4-yl)ethyl]benzamide

The subtitled compound was prepared substantially in accordance with the method detailed in Example 6A using 5.55 g (0.05 mol) of 4-(2-aminoethyl)imidazole in 40 ml ethanol and 8.31 g (0.05 mol) of isatoic anhydride with the exception that after removing ethanol from the reaction solution the product was purified using column chromatography (500 ml dichloromethane; 2000 ml 9% methanol in dichloromethane, isocratic eluent). The fractions containing the desired product were combined and reduced to dryness under reduced pressure to provide a solid. This solid was recrystallized from diethyl ether to provide 1.65 g of the desired subtitled compound (m.p. 85°–87° C.).

Analysis for $C_{12}H_{14}N_4O$: Calc.: C, 62.59; H, 6.13; N, 24.33; Found: C, 62.37; H, 6.23; N, 24.09.

B. N-[2-(1H-Imidazol-4-yl)ethyl]-2-[[3-(trifluoromethyl)benzoyl]benzamide

The titled compound was prepared substantially in accordance with the method detailed in Example 11 using 3.00 g (0.0130 mol) of the subtitled intermediate of Example 28A and 5.43 g (0.026 mol) of m-trifluoromethylbenzoyl chloride with the exception that after removing ethyl acetate the final product was recrystallized from an ethanol/hexane solution to provide 4.6 g of the desired titled compound (m.p. 153°–158° C.).

Analysis for $C_{20}H_{17}F_3N_4O_2$: Calc.: C, 59.70; H, 4.26; N, 13.92; Found: C, 59.99; H, 4.33; N, 13.67.

EXAMPLE 29

N-[2-(1H-Imidazol-4-yl)ethyl]-2-[[[3-(trifluoromethyl)-phenyl]sulfonyl]amino]benzamide

The titled compound was prepared substantially in accordance with the method detailed in Example 1C using 3.00 g (0.0130 mol) of the subtitled intermediate of Example 28A and 3.19 g (0.0130 mol) of m-trifluoromethylbenzenesulfonyl chloride with the exception that after removing ethyl acetate the final product was recrystallized from a methanol/dichloromethane solution to provide 4.01 g of the desired titled compound (m.p. 160°–163° C.).

Analysis for $C_{19}H_{17}F_3N_4O_3S$: Calc.: C, 52.05; H, 3.91; N, 12.78; Found: C, 51.93; H, 3.88; N, 12.89.

EXAMPLE 30

N-[2-(5-Methyl-1H-imidazol-2-yl)ethyl]-2-[[3-(trifluoromethyl)benzoyl]amino]benzamide

A. 2-Amino-N-[2-(5-methyl-1H-imidazol-2-yl)ethyl]benzamide

The subtitled intermediate was prepared substantially in accordance with the method detailed in Example 6A using 9.22 g of (0.0737 mol) of 2-(2-amino-ethyl)-5-methylimidazole and 12.02 g (0.0737 mol) of isatoic anhydride with the exception that after removing isopropanol the residue produced thereby was suspended in a 1:9 methanol/dichloromethane solution and purified by filtration through silica gel. The filtrate was reduced to dryness under reduced pressure and the resultant residue was recrystallized from an ethyl acetate/methanol/hexane solution to provide 10.01 g of the desired subtitled intermediate (m.p. 180°–183.5° C.).

Analysis for $C_{13}H_{16}N_4O$: Calc.: C, 63.92; H, 6.60; N, 22.93; Found: C, 63.93; H, 6.47; N, 22.67.

B. N-[2-(5-Methyl-1H-imidazol-2-yl)ethyl]-2-[[3-(trifluoromethyl)benzoyl]amino]benzamide The titled compound was prepared substantially in accordance with the method detailed in Example 2 using 2.50 g (0.0102 mol) of the subtitled intermediate of Example 30A and 2.13 g (0.0102 mol) of m-trifluoromethyl-benzoyl chloride with the exception that after removing ethyl acetate from the reaction mixture the residue produced thereby was suspended in a 19:1 dichloromethane/methanol solution and then purified by filtration through silica gel. The filtrate was reduced to dryness under reduced pressure and the resultant residue was recrystallized from a propanone/hexane solution to provide 2.94 g of the desired titled compound (m.p. 168°–172° C.).

Analysis for $C_{21}H_{19}F_3N_4O_2$: Calc.: C, 60.57; H, 4.60; N, 13.46; Found: C, 60.65; H, 4.55; N, 13.26.

EXAMPLE 31

N-[2-(2-Methyl-(1H-imidazol-4-yl)ethyl]-2-[[4-(1,1-dimethylethyl)benzoyl]amino]benzamide monohydrochloride

A. 2-Amino-N-[2-(2-methyl-1H-imidazol-4-yl)ethyl]-benzamide dihydrochloride

The subtitled intermediate was prepared substantially in accordance with the method detailed in Example 6A using 6.26 g (0.05 mol) of 2-methylhistamine dihydrochloride and 8.16 g (0.05 mol) of isatoic anhydride with the exception that after separating the organic and aqueous phases the aqueous phase was extracted with diethyl ether. The diethyl ether extract was then washed with a saturated sodium chloride solution, dried with anhydrous sodium sulfate and reduced to dryness under reduced pressure to provide an oil. This oil was dissolved in an ethanol/diethyl ether solution which was reduced to dryness under reduced pressure to provide a solid. This solid was then recrystallized from a methanol/diethyl ether solution to provide 13.69 g of the desired subtitled intermediate (m.p. 221°–252° C.).

Analysis for $C_{13}H_{16}N_4O \cdot 2HCl$: Calc.: C, 49.22; H, 5.72; N, 17.66; Found: C, 48.58; H, 5.86; N, 17.39.

B. N-[2-(2-Methyl-1H-imidazol-4-yl)ethyl]-2-[[4-(1,1-dimethylethyl)benzoyl]amino]benzamide monohydrochloride The titled compound was prepared substantially in accordance with the method detailed in Example 15 using 2.50 g (0.00788 mol) of the subtitled intermediate of Example 31A and 3.16 g (0.01576 mol) of p-tert-butylbenzoyl chloride with the exception that the final product was recrystallized from a cyanomethane/methanol solution to provide 2.68 g of the desired titled compound (m.p. 237°–239.5° C.).

Analysis for $C_{24}H_{28}N_4O_2 \cdot HCl$: Calc.: C, 65.37; H, 6.62; N, 12.70; Found: C, 65.52; H, 6.72; N, 12.56.

EXAMPLE 32

N-[2-(2-Methyl-1H-imidazol-4-yl)ethyl]-2-[[3-(trifluoromethyl)benzoyl]amino]benzamide monohydrochloride

The titled compound was prepared substantially in accordance with the method detailed in Example 15 using 2.30 g (0.00725 mol) of the subtitled intermediate of Example 31A and 3.41 g (0.0145 mol) of m-trifluoromethylbenzoyl chloride with the exception that the final product was recrystallized from diethyl ether containing a small amount of ethanol to provide 3.11 g of the desired titled compound (m.p. 209°–212° C.).

Analysis for $C_{21}H_{19}F_3N_4O_2 \cdot HCl$: Calc.: C, 55.70; H, 4.45; N, 12.37; Found: C, 55.99; H, 4.40; N, 12.13.

EXAMPLE 33

N-[2-(2-Methyl-1H-imidazol-4-yl)ethyl]-2-[[[3-(trifluoromethyl)phenyl]sulfonyl]amino]benzamide monohydrochloride The titled compound was prepared substantially in accordance with the method detailed in Example 6B using 2.30 g (0.00725 mol) of the subtitled intermediate of Example 31A and 4.01 g (0.0145 mol) of m-trifluoromethylbenzenesulfonyl chloride with the exception that after removing ethyl acetate the resultant oil was purified using column chromatography (8000 ml of a gradient eluent of 0–10% methanol in a 1% ammonia in dichloromethane solution). The fractions containing the desired product were combined and reduced to dryness under reduced pressure to provide a foam. This foam was recrystallized from an ethanol/diethyl ether solution to provide a solid. This solid was dissolved in methanol containing diethyl ether and hydrochloric acid. The resultant solution was reduced to dryness under reduced pressure to provide a foam which was then recrystallized from a propanone/diethyl ether solution to provide 2.81 g of the desired titled compound (m.p. 150°–155° C.).

Analysis for $C_{20}H_{19}F_3N_4O_3S \cdot HCl$: Calc.: C, 49.13; H, 4.12; N, 11.46; Found: C, 48.93; H, 4.11; N, 11.29.

EXAMPLE 34

N-[2-(2-Methyl-1H-imidazol-4-yl)ethyl]-2-[[(4-chlorophenyl)sulfonyl]amino]benzamide monohydrochloride The titled compound was prepared substantially in accordance with the method detailed in Example 6B using 2.30 g (0.00725 mol) of the subtitled intermediate of Example 31A and 3.56 g (0.0145 mol) of 4-chlorobenzenesulfonyl chloride with the exception that after removing ethyl acetate the resultant solid was dissolved in methanol containing diethyl ether and hydrochloric acid. The resultant solution was reduced to dryness under reduced pressure to provide a solid which was recrystallized from cyanomethane, ground in a mortar and dried under vacuum at 100° C. for 5 hours to provide 1.87 g of the desired titled compound (m.p. 159°–167° C.).

Analysis for $C_{19}H_{19}ClN_4O_3S \cdot HCl$: Calc.: C, 50.12; H, 4.43; N, 12.30; Found: C, 50.14; H, 4.58; N, 12.35.

EXAMPLE 35

N-[2-(2-Thiazolyl)ethyl]-2-[[(4-chlorophenyl)sulfonyl]amino]benzamide oxalate

A. 2-Amino-N-[2-(2-thiazolyl)ethyl]benzamide dihydrochloride

The subtitled intermediate was prepared substantially in accordance with the method detailed in Example 6A using 7.20 g (0.0562 mol) of 2-(2-aminoethyl)-thiazole and 9.20 g (0.0562 mol) of isatoic anhydride with the exception that after removing ethyl acetate the resultant solid was dissolved in methanol containing diethyl ether and hydrochloric acid. The resultant solution was reduced to dryness under reduced pressure to provide a solid which was purified by crystallization from an ethanol/ethyl acetate solution, followed by recrystallization from a methanol/ethyl acetate/diethyl ether solution, to provide 9.25 g of the desired subtitled intermediate (m.p. 201°–227° C.).

Analysis for $C_{12}H_{13}N_3OS \cdot 2HCl$: Calc.: C, 45.01; H, 4.72; N, 13.12; Cl, 22.14; Found: C, 44.93; H, 4.76; N, 12.99; Cl, 21.90.

B. N-[2-(2-Thiazolyl)ethyl]-2-[[(4-chlorophenyl)-sulfonyl]amino]benzamide oxalate The titled compound was prepared substantially in accordance with the method detailed in Example 1C using 2.00 g (0.00625 mol) of the subtitled intermediate of Example 35A and 1.49 g (0.00687 mol) of 4-chlorobenzenesulfonyl chloride with the exception that after separating the organic and aqueous layers the organic layer was washed with a saturated sodium chloride solution, dried with anhydrous sodium sulfate and then reduced to dryness under reduced pressure to provide an oil. This oil was suspended in ethyl acetate and purified by filtration through silica gel. The filtrate was reduced to dryness under reduced pressure to provide an oil. This oil was dissolved in methanol and 0.5625 g (0.00625 mol) of oxalic acid were added. The resulting solution was reduced to dryness under reduced pressure to provide a solid which was purified by crystallization from an ethyl acetate/hexane solution, followed by crystallization from an ethanol/hexane solution, to provide 2.19 g of the desired titled compound (m.p. 133°–137° C.).

Analysis for $(C_{18}H_{17}ClN_3O_3S_2)_2 \cdot C_2H_2O_4$: Calc.: C, 48.77; H, 3.88; N, 8.98; S, 13.70; Found: C, 49.20; H, 3.61; N, 9.03; S, 13.54.

EXAMPLE 36

N-[2-(2-Thiazolyl)ethyl]-2-[(4-chlorobenzoyl)amino]-benzamide

The titled compound was prepared substantially in accordance with the method detailed in Example 2 using 2.00 g (0.00625 mol) of the subtitled intermediate of Example 35A and 1.21 g (0.00687 mol) of 4-chlorobenzoyl chloride with the exception that after removing ethyl acetate the resultant solid was purified by recrystallization from an ethanol/diethyl ether solution to provide 2.23 g of the desired titled compound (m.p. 156°–159.5° C.).

Analysis for $C_{19}H_{16}ClN_3O_2S$: Calc.: C, 59.14; H, 4.18; N, 10.87; Found: C, 58.90; H, 4.15; N, 10.73.

EXAMPLE 37

N-[3-(Dimethylamino)propyl]-2-[[4-(1,1-dimethylethyl)-benzoyl]amino]benzamide oxalate A. 2-Amino-N-[3-(dimethylamino)propyl]benzamide dihydrochloride The subtitled intermediate was prepared substantially in accordance with the method detailed in Example 6A using 33.4 g (0.323 mol) of 3-dimethylamino-propylamine and 52.7 g (0.323 mol) of isatoic anhydride with the exception that after separating the organic and aqueous layers the organic layer was washed with a saturated sodium chloride solution, dried with anhydrous sodium sulfate and reduced to dryness under reduced pressure to provide an oil. This oil was dissolved in 500 ml of methanol containing diethyl ether and hydrochloric acid and then heated on a steam bath for approximately ¼ hour. The resultant hot mixture was filtered and 1000 ml of diethyl ether were added to the filtrate. The resultant mixture was filtered providing 77.3 g of a solid (m.p. 203°–209° C.).

Analysis for $C_{12}H_{19}N_3O \cdot 2HCl$: Calc.: C, 48.99; H, 7.19; N, 14.28; Found: C, 49.62; H, 7.39; N, 14.50.

B. N-[3-(Dimethylamino)propyl]-2-[[4-1,1-dimethylethyl)benzoyl]benzoyl]amino]benzamide oxalate The titled compound was prepared substantially in accordance with the method detailed in Example 2 using 5.00 g (0.017 mol) of the subtitled intermediate of Example 37A and 3.90 g (0.0194 mol) of p-tert-butylbenzoyl chloride with the exception that after separating the organic and aqueous layers the organic layer was washed with a saturated sodium chloride solution, dried with anhydrous sodium sulfate and reduced to dryness under reduced pressure to provide an oil. This oil was dissolved in methanol and 1.6 g (0.0178 mol) of oxalic acid were added. The resulting solution was reduced to dryness under reduced pressure to provide a solid. This solid was purified by crystallization from an ethyl acetate/diethyl ether solution followed by recrystallization from an ethyl acetate/methanol solution, to provide 6.34 g of the desired titled compound (m.p. 152°–155° C.).

Analysis for $C_{23}H_{31}N_3O_2 \cdot C_2H_2O_4$: Calc.: C, 63.68; H, 7.05; N, 8.91; Found: C, 63.66; H, 7.06; N, 8.91.

EXAMPLE 38

N-[3-(Dimethyl amino)propyl]-2-[[[3-(trifluoromethyl)-phenyl]sulfonyl]amino]benzamide The titled compound was prepared substantially in accordance with the method detailed in Example 35B using 5.00 g (0.017 mol) of the subtitled intermediate of Example 37A and 4.75 g (0.0194 mol) of 3-trifluoromethylbenzenesulfonyl chloride with the exception that after removing ethyl acetate the resultant residue was substantially dissolved in boiling ethanol and then filtered hot. The filtrate was reduced to dryness under reduced pressure to provide a solid. This solid was purified by crystallization from ethyl acetate, followed by recrystallization from an ethanol/hexane solution, to provide 4.02 g of the desired titled compound (m.p. 116°–123° C.).

Analysis for $C_{19}H_{22}F_3N_3O_3S$: Calc.: C, 53.14; H, 5.16; N, 9.78; Found: C, 52.47; H, 5.14; N, 9.32.

EXAMPLE 39

N-[(1H-Imidazol-2-yl)methyl]-2-[[3-(trifluoromethyl)-benzoyl]amino]benzamide hydrochloride A. 2-Amino-N-[(1-trityl-1H-imidazol-2-yl)methyl]-benzamide Isatoic anhydride (2.65 g; 0.0162 mol) was slowly added to a room temperature solution of 5.51 g (0.0162 mol) of 2-(aminomethyl)-1-tritylimidazole in 30 ml of methylene chloride and 65 ml of isopropanol. The reaction mixture was then allowed to react overnight. The next morning the solution was reduced to dryness under reduced pressure and the resultant residue was redissolved in an ethyl acetate/aqueous sodium bicarbonate mixture. The resulting layers were separated, the organic layer was washed with water and then a saturated sodium chloride solution, dried over anhydrous sodium sulfate and finally reduced to dryness to provide a yellow solid. This solid was filtered through silica gel using 1000 ml of methylene chloride followed by 1000 ml of a 2% methanol in methylene chloride solution. The resulting filtrate was reduced to dryness to provide a white solid. This solid was recrystallized from a 1:1 ethyl acetate/hexanes solution to provide 5.95 g of the desired subtitled intermediate (m.p 171°–175° C.).

Analysis for $C_{30}H_{26}N_4O$ Calc.: C, 78.52; H, 5.71; N, 12.22; Found: C, 78.29; H, 5.76; N, 12.38.

B. N-[(1-Trityl-1H-imidazol-2-yl)methyl]-2-[[3-(trifluoromethyl)benzoyl]amino]-benzamide The subtitled compound was prepared substantially in accordance with the method detailed in Example 37B using 5.3 g (0.012 mol) of the subtitled intermediate of Example 39A and 2.65 g (0.0132 mol) of m-trifluoromethylbenzoyl chloride, with the exception that after reducing the organic layer to dryness under reduced pressure the resulting oil was dissolved in approximately 1 liter of a hot solution of ethyl acetate containing a small amount of methanol. The solution was then filtered through silica gel and the resulting filtrate was reduced to a volume of approximately 250 ml under reduced pressure. Solids which had precipitated were removed by filtration and the resulting filtrate was reduced to dryness to provide 6.09 g of a solid containing the desired subtitled intermediate.

C. N-[(1H-Imidizol-2-yl)methyl]-2-[[3-(trifluoromethyl)benzoyl]amino]benzamide hydrochloride The subtitled intermediate of Example 39B (6.0 g; 0.0095 mol) was slurried in a methanol/water solution and then 150 ml of 3N hydrochloric acid were added, while heating. Once all solids dissolved, the resulting solution was reduced in volume under reduced pressure while solids precipitated. These solids were recovered by filtration and recrystallized (twice) from an ethanol/diethyl ether solution to provide 2.59 g of the desired titled compound (m.p. 209°–213° C.).

Analysis for $C_{19}H_{15}F_3N_4O_2 \cdot HCl$: Calc.: C, 53.72; H, 3.79; N, 13.19; Found: C, 53.98; H, 3.88; N, 13.00.

EXAMPLE 40

N-[(1H-Imidazol-2-yl)methyl]-2-[[[3-(trifluoromethyl)-phenyl]sulfonyl]amino]benzamide hydrochloride A. N-[(1-Trityl-1H-imidazol-2-yl)methyl]-2-[[[3-(trifluoromethyl)phenyl]sulfonyl]amino]benzamide The subtitled intermediate was prepared substantially in accordance with the method detailed in Example 39B using 5.3 g (0.012 mol) of 2-amino-N-[(1-trityl-1H-imidazol-2-yl)methyl]benzamide (prepared as in Example 39A) and 3.0 g (0.012 mol) of m-trifluoromethylbenzoylsulfonyl chloride, with the exception that after reducing the organic layer to dryness under reduced pressure the resulting oil was dissolved in methylene chloride and then filtered through silica gel while eluting with 2500 ml of methylene chloride followed by 2000 ml of a 2% methanol in methylene chloride solution. Fractions containing the desired subtitled intermediate were combined and reduced to dryness under reduced pressure to provide a foam. This foam crystallized upon addition to hot methanol and the crystals were then recovered to provide 6.24 g of a solid containing primarily the desired subtitled intermediate (m.p. 101°–106° C.).

Analysis for $C_{37}H_{29}F_3N_4O_3S$: Calc.: C, 66.66; H, 4.38; N, 8.40; Found: C, 68.81; H, 4.68; N, 8.50.

B. N-[(1H-Imidazol-2-yl)methyl]-2-[[[3-(trifluoromethyl)phenyl]sulfonyl]amino]benzamide hydrochloride The subtitled intermediate from Example 40A (6.11 g; 0.0092 mol) was converted to 3.29 g of the desired titled compound substantially in accordance with the procedure detailed in Example 39C (m.p. 228°–237° C.).

Analysis for $C_{18}H_{15}F_3N_4O_3S \cdot HCl$: Calc.: C, 46.91; H, 3.50; N, 12.16; Found: C, 47.18; H, 3.67; N, 12.40.

EXAMPLE 41

N-[3-(1H-Imidazol-2-yl)propyl]-2-[[3-(trifluoromethyl)-benzoyl]amino]benzamide hydrochloride monohydrate A. 2-Amino-N-[3-(1-trityl-1H-imidazol-2-yl)-propyl]-benzamide The subtitled compound was prepared substantially in accordance with the method detailed in Example 39A using 16.5 g (0.0449 mol) of 2-(3-aminopropyl)-1-tritylimidazole and 7.5 g (0.046 mol) of isatoic anhydride, with the exception that after reducing the organic layer to dryness under reduced pressure to provide a solid the solid was filtered through silica gel using 3000 ml of methylene chloride followed by 4000 ml of a 2% methanol in methylene chloride solution. The resulting filtrate was reduced to dryness under reduced pressure to provide a foamy oil. This oil was dissolved in 1000 ml of boiling ethanol. The resulting solution was then reduced under reduced pressure to approximately 200 ml in volume and then cooled to 0° C. while solids precipitated. These solids were recovered by filtration and washed with ethanol to provide 18.6 g of the desired subtitled intermediate (m.p. 198.5°–207° C.).

Analysis for $C_{32}H_{30}N_4O$ Calc.: C, 78.99; H, 6.21; N, 11.51; Found: C, 80.19; H, 6.41; N, 11.71.

B. N-[3-(1-Trityl-1H-imidazol-2-yl)propyl]-2-[[3-(trifluoromethyl)benzoyl]amino]-benzamide The subtitled intermediate was prepared substantially in accordance with the method detailed in Example 40A using 5.6 g (0.0115 mol) of the subtitled intermediate of Example 41A and 2.46 g (0.0115 mol) of m-trifluoromethylbenzoyl chloride, with the exception that after reducing the organic layer to dryness under reduced pressure the resulting oil was dissolved in a solution containing approximately 100 ml of methylene chloride and a few milliliters of methanol. The resulting solution was then filtered through silica gel while eluting with 2250 ml of methylene chloride. Fractions containing the desired subtitled intermediate were combined and reduced to dryness under reduced pressure to provide 7.3 g of the desired subtitled intermediate (m.p. 187°–190° C.).

Analysis for $C_{40}H_{33}F_3N_4O_2$: Calc.: C, 72.94; H, 5.05; N, 8.51; Found: C, 73.22; H, 5.33; N, 8.76.

C. N-[3-(1H-Imidazol-2-yl)propyl]-2-[[3-(trifluoromethyl)benzoyl]amino]benzamide hydrochloride monohydrate The subtitled intermediate of Example 41 B (7.3 g) was slurried in a methanol/water solution and then 50 ml of 3N hydrochloric acid were added, while heating. After heating for 30 minutes most of the solids had dissolved. The hot suspension was then filtered to remove any undissolved solids and the resulting filtrate was reduced to dryness under reduced pressure to provide an oil. This oil was substantially dissolved in an ethanol/diethyl ether solution. The resulting suspension was filtered to remove undissolved solids, after which the filtrate was reduced to dryness under reduced pressure to provide a gum. This gum was dissolved in methylene chloride containing a small amount of methanol and the resulting solution was filtered through silica gel while eluting with 500 ml of methylene chloride and then a 5% methanol in methylene chloride solution. Fractions containing the desired titled compound were combined and then reduced to dryness under reduced pressure to provide an amorphous solid. This solid was heated to 80° C. under 0.1 mm Hg vacuum for 6 hours, after which 2.3 g of an amorphous solid were obtained. This solid assayed as the desired titled compound (m.p. 93°–105° C.).

Analysis for $C_{21}H_{19}F_3N_4O_2 \cdot HCl \cdot H_2O$: Calc.: C, 53.57; H, 4.71; N, 11.90; Found: C, 53.59; H, 4.49; N, 11.70.

EXAMPLE 42

N-[3-(1H-Imidazol-2-yl)propyl]-2-[[[3-(trifluoromethyl)-phenyl]sulfonyl]amino]benzamide hydrochloride monohydrate A. N-[3-(1-Trityl-1H-imidazol-2-yl)propyl]-2-[[[3-(trifluoromethyl)phenyl]sulfonyl]amino]benzamide The subtitled intermediate was prepared substantially in accordance with the method detailed in Example 40A using 5.6 g (0.0115 mol) of 2-amino-N-[3-(1-trityl-1H-imidazol-2-yl)propyl]benzamide (prepared as in Example 41A) and 2.88 g (0.0115 mol) of m-trifluoromethylbenzenesulfonyl chloride, with the exception that the oil/methylene chloride solution was filtered through silica gel while eluting with 2500 ml of methylene chloride followed by 6000 ml of a 0.5–5% gradient of methanol in methylene chloride. Fractions containing the desired subtitled intermediate were combined and reduced to dryness under reduced pressure to provide a solid. This solid was triturated with 80 ml of diethyl ether and the liquid from the trituration was combined with 50 ml of hexanes. The resulting solution was concentrated to a volume of approximately 30 ml, after which additional hexane was added until a two-phase solution resulted. The two-phase solution was reduced to dryness under reduced pressure to provide a solid. This solid was recrystallized from an ethanol/methanol solution to provide 2.35 g of the desired subtitled intermediate (m.p. 163°–170° C.).

Analysis for $C_{39}H_{33}F_3N_4O_3S$: Calc.: C, 67.42; H, 4.79; N, 8.06; Found: C, 67.54; H, 4.91; N, 7.80.

N-[3-(1H- Imidazol-2-yl)propyl]-2-[[[3-(trifluoromethyl)phenyl]sulfonyl]amino]-benzamide hydrochloride monohydrate The subtitled intermediate of Example 42A (2.1 g) was slurried in methanol while 50 ml of a 3N hydrochloric acid solution were added, while heating. The resulting solution was heated for 30 minutes and then reduced to dryness under reduced pressure to provide an oily gum. The gum was triturated with 30 ml of diethyl ether and the resulting liquid was reduced to dryness under reduced pressure to provide an oil. This oil was dissolved in methanol and then filtered through silica gel while eluting with 1000 ml of methylene chloride, 1000 ml of a 2% methanol in methylene chloride solution and then finally 3000 ml of a 5% methanol in methylene chloride solution. Fractions containing the desired titled compound were combined and then reduced to dryness under reduced pressure to provide an oil. This oil was dried under vacuum (0.1 mm Hg) at 63° C. for 6 hours to provide the desired titled compound as an amorphous solid (m.p. 70°–115° C.). Analysis for $C_{20}H_{19}F_3N_4O_3S \cdot HCl \cdot H_2O$: Calc.: C, 47.39; H, 4.37, N, 11.05; Found: C, 47.48; H, 4.09, N, 10.84.

EXAMPLE 43

N-[3-(1H-Imidazol-2-yl)propyl]-2-[[4-(1,1-dimethylethyl)-benzoyl]amino]benzamide hydrochloride monohydrate A. N-[3-(1-Trityl-1H-imidazol-2-yl)propyl]-2-[[4-(1,1-dimethylethyl)benzoyl]amino]-benzamide The subtitled intermediate was prepared substantially in accordance with the method detailed in Example 40A using 5.6 g (0.0115 mol) of 2-amino-N-[3-(1-trityl-1H-imidazol-2-yl)propyl]benzamide (prepared as in Example 41A) and 2.35 g (0.0115 mol) of 98% para-t-butylbenzoyl chloride, with the exception that the oil/methylene chloride solution was filtered through silica gel while eluting with 1000 ml of methylene chloride, 2000 ml of a 2% methanol in methylene chloride solution and then 1500 ml of a 5% methanol in methylene chloride solution. Fractions containing the desired subtitled intermediate were combined and reduced to dryness to provide a foam. This foam was crystallized from a methylene chloride/hexanes solution to provide a solid. This solid was recrystallized from a methylene chloride/methanol/hexanes solution to provide 1.86 g of the desired subtitled intermediate (m.p. 219°–223° C.).

Analysis for $C_{43}H_{42}N_4O_2$: Calc.: C, 79.85; H, 6.54; N, 8.66; Found: C, 80.46; H, 6.73; N, 8.93.

N-[3-(1H-Imidazol-2-yl)propyl]-2-[[4-(1,1-dimethylethyl)benzoyl]amino]benzamide hydrochloride monohydrate The subtitled intermediate of Example 43A (1.74 g) was slurried in methanol and then 50 ml of 3N hydrochloric acid were added, while heating. After heating for 30 minutes most of the solids had dissolved. The hot suspension was then filtered to remove any undissolved solids and the resulting filtrate was reduced to dryness under reduced pressure to provide an oil. This oil was dissolved in methylene chloride containing a trace amount of methanol and the resulting solution was then filtered through silica gel while eluting with a 0–5% methanol in methylene chloride gradient. Fractions containing the desired title compound were combined and reduced to dryness under reduced pressure to provide a foam. This foam was crystallized by dissolving it in a methanol/ethyl acetate solution and then concentrating the resulting solution until cloudiness developed. The cloudy solution was cooled to room temperature and then seeded with authentic titled compound. After 1¼ hours solids precipitated. These solids were recovered by filtration and washed with ethyl acetate to provide 0.84 g of the desired titled compound (m.p. 163.5°–170° C.).

Analysis for $C_{24}H_{28}N_4O_2 \cdot HCl \cdot H_2O$: Calc.: C, 62.80; H, 6.81; N, 12.21; Found: C, 62.04; H, 6.52; N, 12.35.

EXAMPLE 44

N-[(1H-Imidazol-2-yl)methyl]-2-[[4-(1,1-dimethylethyl)-benzoyl]amino]benzamide hydrochloride A. N-[(1-Trityl-1H-imidazol-2-yl)methyl]-2-[[4-(1,1-dimethylethyl)benzoyl]amino]benzamide The subtitled intermediate was prepared substantially in accordance with the method detailed in Example 39B using 5.3 g (0.012 mol) of 2-amino-N-[(1-trityl-1H-imidazol-2-yl)methyl]benzamide (prepared as in Example 39A) and 2.5 g (0.012 mol) of 98% pure para-t-butylbenzoyl chloride, with the exception that after reducing the organic layer to dryness under reduced pressure the resulting oil was substantially dissolved in 300 ml of methylene chloride. Any solids which did not dissolve were removed by filtration (1.21 g) and set aside. The filtrate from the filtration was reduced under reduced pressure to approximately 100 ml in volume and then filtered through silica gel while eluting with 2500 ml of methylene chloride followed by 2000 ml of a 5% methanol in methylene chloride solution. Fractions containing the desired subtitled intermediate were reduced to dryness under reduced pressure and the resulting solid was triturated in 20 ml of methanol to provide 0.9 g of a white solid. A portion of this solid (0.3 g) was recrystallized from a methylene chloride/methanol solution to provide 0.17 g of the desired subtitled intermediate (m.p. 202°–205° C.).

Analysis for $C_{41}H_{38}N_4O_2$: Calc.: C, 79.58; H, 6.39; N, 8.93; Found: C, 79.37, H, 6.17; N, 9.18.

N-[(1H-Imidazol-2-yl)methyl]-2-[[4-(1,1-dimethylethyl)benzoyl]amino]benzamide hydrochloride The solids which were set aside in Example 44A (1.21 g) and the remainder of the product of Example 44A (0.6 g) were combined and then dissolved in methanol while 30 ml of 3N hydrochloric acid were added, with heating. After all solids had dissolved the resulting solution was reduced to dryness under reduced pressure to provide a residue. This residue was substantially dissolved in ethanol and any undissolved material was removed by filtration. The filtrate from the filtration was mixed with methylene chloride and the resulting solution was filtered through silica gel while eluting with 2500 ml of methylene chloride followed by 1000 ml of a 2–5% methanol in methylene chloride gradient. Fractions containing the desired titled compound were combined and then purified using standard purification techniques to provide 2.18 g of the desired titled compound (m.p. 192°–197° C.).

Analysis for $C_{22}H_{24}N_4O_2 \cdot HCl$: Calc.: C, 63.99; H, 6.10; N, 13.57; Found: C, 63.78; H, 6.12; N, 13.66.

EXAMPLE 45

N'-Methyl-N-[2-(1H-imidazol-2-yl)ethyl]-2-[[3-(trifluoromethyl)benzoyl]amino]benzamide hydrochloride A. N-Methyl-N-[3-(trifluoromethyl)benzoyl]methyl anthranilate To a cold (0° C.) solution of 53.5 g (0.324 mol) of N-methyl methyl anthranilate and 50 ml (0.359 mol) of triethylamine in 350 ml of methylene chloride were added, over a period of 30 minutes, 67.82 g (0.325 mol) of m-trifluoromethylbenzoyl chloride. The resulting solution was warmed to room temperature and then stirred for 72 hours. Water was then added to the reaction solution. The resulting layers were separated and the organic layer was washed successively with a 0.1N hydrochloric acid solution, a saturated sodium bicarbonate solution and water and then reduced to dryness to provide an oil. This oil was filtered through silica gel while eluting with 2635 ml of methylene chloride followed by 2000 ml of a 10–20% methanol in methylene chloride gradient. Fractions containing the desired subtitled intermediate were combined and then re-chromatographed on a silica gel column while eluting with a 50–86% methylene chloride in hexane gradient. Fractions containing the desired subtitled intermediate were combined and reduced to dryness under reduced pressure to provide 20.8 g of an oil. Thin layer chromatography indicated this oil was substantially the desired subtitled intermediate.

B. N-Methyl-N-[3-(trifluoromethyl)benzoyl]anthranilic acid

A portion of the intermediate from Example 45A (11.69 g; 0.0347 mol) was dissolved in 50 ml of methanol and 40 ml of 1N sodium hydroxide were added. The resulting solution was heated to 60° C., stirred at that temperature for 10 minutes, cooled to room temperature and then stirred for 72 hours. After 72 hours, some of the methanol was removed under reduced pressure and then 43 ml of 1N hydrochloric acid were added, with stirring. A white solid precipitated and was recovered by filtration, washed with water and then dried under vacuum at 80° C. to provide 10.98 g of the desired subtitled intermediate (m.p. 144°–145.5° C.).

Analysis for $C_{16}H_{12}NO_3F_3$: Calc.: C, 59.45; H, 3.74; N, 4.33; Found: C, 59.55; H, 3.66; N, 4.35.

C. N-Methyl-N-[2-(1H-imidazol-2-yl)ethyl]-2-[[3-(trifluoromethyl)benzoyl]amino]benzamide hydrochloride To a cold (5° C.) solution of the subtitled intermediate of Example 45B (8.0 g; 0.0247 mol) in 20 ml of dimethylformamide was added a solution of 1,1'-carbonyldiimidazole (4.05 g; 0.025 mol) in 30 ml of dimethylformamide. The resulting solution was allowed to warm to room temperature and then stirred for 3 hours at that temperature.

Meanwhile, to a solution of 4.56 g (0.0247 mol) of 2-(2-aminoethyl)imidazole dihydrochloride dissolved in water were added 49.5 ml of 1N sodium hydroxide. The resulting solution was reduced to dryness under reduced pressure and the resultant residue was washed three times with an ethanol/toluene solution to remove residual water. The residue was then dissolved in 20 ml of dimethylformamide.

The two solutions prepared above were combined and stirred at room temperature overnight. The next morning, volatiles were removed under reduced pressure and the resultant residue was dissolved in an ethyl acetate/aqueous sodium bicarbonate solution. The organic layer was separated from the resulting two-phase solution and then washed several times with water, dried over anhydrous sodium sulfate and reduced to dryness under reduced pressure to provide an oil. A portion of this oil was crystallized from a 95:5 diethyl ether/ethanol solution. The filtrate from the crystallization step was reduced to dryness under reduced pressure to provide a gum. This gum was purified using preparatory high performance liquid chromatography (8000 ml of a gradient of methylene chloride to 10% methanol and 1% ammonium hydroxide in methylene chloride). Fractions containing the free base form of the desired titled compound were combined and then reduced to dryness under reduced pressure to provide a yellow solid. This solid was dissolved in methanol and a concentrated hydrochloric acid/diethyl ether solution was added. The resulting solution was reduced to dryness under reduced pressure to provide a residue, which residue was then recrystallized from ethanol to provide 1.58 g of the desired titled compound (m.p. 210°–216° C.).

Analysis for $C_{21}H_{19}F_3N_4F_3N_4O_2 \cdot HCl$: Calc.: C, 55.70; H, 4.45; N, 12.37; Found: C, 55.83; H, 4.45; N, 12.15

EXAMPLE 46

N-[2-[[[2-(1H-Imidazol-2-yl)ethyl]amino]sulfonyl]phenyl]-3-(1,1-dimethylethyl)benzamide oxalate The titled compound was prepared substantially in accordance with the method detailed in Example 1C using 2.80 g (0.0107 mol) of 2-amino-N-[2-(1H-imidazol-2-yl)-ethyl] benzene sulfonamide and 4.20 g (0.0213 mol) of meta-t-butylbenzoyl chloride with the exception that, after reducing the reaction solution to dryness under reduced pressure the resultant residue was dissolved in methanol. The resulting solution was heated to reflux for approximately one hour and then reduced to dryness under reduced pressure. The resultant residue was redissolved in an ethyl acetate/aqueous sodium bicarbonate mixture. The resulting layers were separated and the organic layer was washed with water and then a saturated sodium chloride solution, dried over anhydrous sodium sulfate and then reduced to dryness under reduced pressure. The resultant residue was purified using preparatory high performance liquid chromatography (8000 ml of a gradient of methylene chloride to 10% methanol and 0.5% ammonium hydroxide in methylene chloride). Fractions containing the free base form of the desired titled compound were combined and then reduced to dryness under reduced pressure to provide an oil. This oil was dissolved in methanol and 0.36 g of oxalic acid were added, with stirring. The resulting solution was reduced to dryness under reduced pressure to provide a foam. This foam was crystallized from a 1:10 solution of methanol/ethyl acetate to provide 1.74 g of the desired titled compound (m.p. 191°–193.5° C.).

Analysis for $C_{22}H_{26}N_4O_3S \cdot C_2H_2O_4$: Calc.: C, 58.58; H, 5.77; N, 11.88; Found: C, 58.78; H, 5.79; N, 11.65.

EXAMPLE 47

N-[2-(1H-Imidazol-2-yl)ethyl]-2-[[3-(1,1-dimethylethyl)-benzoyl]amino]benzamide

The titled compound was prepared substantially in accordance with the method detailed in Example 46 using 2.50 g (0.0107 mol) of 2-amino-N-[2-(1H-imidazol-2-yl)ethyl]benzamide and 4.20 g (0.0213 mol) of meta-t-butylbenzoyl chloride with the exception that, after reducing the organic layer to dryness the resulting residue was dissolved in a 1:7 methanol/ethyl acetate solution. The resulting solution was concentrated until crystals began to form and then diethyl ether was added. The resulting solution was cooled and 2.90 g of the desired titled compound were recovered by filtration (m.p. 205°–210° C.).

Analysis for $C_{23}H_{26}N_4O_2$: Calc.: C, 70.47; H, 6.71; N, 14.35; Found: C, 70.63; H, 6.53; N, 14.57.

EXAMPLE 48

N'-Methyl-N-[2-(1H-imidazol-2-yl)ethyl]-2-[[4-(1,1-dimethylethyl)benzoyl]amino]benzamide hydrochloride A. N-Methyl-N-[4-(1,1-dimethylethyl)benzoyl]-methyl anthranilate The subtitled intermediate was prepared substantially in accordance with the method detailed in Example 45A using 51.81 g (0.314 mol) of N-methyl methyl anthranilate, 61.52 g (0.313 mol) of para-t-butylbenzoyl chloride and 50 ml (0.359 mol) of triethylamine with the exception that, after the organic layer was reduced to dryness the resultant oil was dissolved in 500 ml of hot (refluxing) cyclohexane. The resulting solution was cooled to room temperature and 85.3 g of the desired subtitled intermediate were recovered by filtration (m.p. 93.5°–94.5° C.).

B. N-Methyl-N-[4-(1,1-dimethylethyl)benzoyl]anthranilic acid

The subtitled intermediate was prepared substantially in accordance with the method detailed in Example 45B using 32.5 g (0.1 mol) of the intermediate of Example 45A, 120 ml of 1N sodium hydroxide and 150 ml of 1N hydrochloric acid to provide 30.2 g of the desired subtitled intermediate (m.p. 172.5°–175° C.).

Analysis for $C_{19}H_{21}NO_3$: Calc.: C, 73.20; H, 6.80; N, 4.50; Found: C, 73.57; H, 6.82, N, 4.47.

C. N'-Methyl-N-[2-(1H-imidazol-2-yl)ethyl]-2-[[4-(1,1-dimethylethyl)benzoyl]amino]benzamide hydrochloride The titled compound was prepared substantially in accordance with the method detailed in Example 45C using 5.51 g (0.0177 mol) of the intermediate of Example 45B, 2.92 g (0.018 mol) of 1,1'-carbonyldiimidazole and 3.62 g (0.0177 mol) of 2-(2-aminoethyl)imidazole dihydrochloride with the exception that, after the organic layer was reduced to dryness to provide a foam the foam was purified by preparatory high performance liquid chromatography (8000 ml of a gradient of methylene chloride to 10% methanol and 1% ammonium hydroxide in methylene chloride). Fractions containing the free base form of the desired titled compound were combined and reduced to dryness under reduced pressure. The resultant oily foam was crystallized from a methylene chloride/hexane solution to provide a white solid. This solid was dissolved in methanol and a concentrated hydrochloric acid/diethyl ether solution was added. The resulting solution was reduced to dryness under reduced pressure to provide a foam. This foam was purified by dissolving it in 55 ml of a 3:1 diethyl ether/ethanol solution and then, after dissolution had been obtained, adding an additional 50 ml of diethyl ether. The resultant gummy precipitate was removed by filtration and the filtrate was reduced to dryness under reduced pressure to provide an oil. This oil was recrystallized from diethyl ether to provide 2.08 g of the desired titled compound (m.p. 124°–132° C.).

Analysis for $C_{29}H_{28}N_4O_2 \cdot HCl$: Calc.: C, 63.92; H, 6.63; N, 12.70; Found: C, 65.25; H, 6.87; N, 13.00.

The present invention provides a method for lowering blood glucose levels in mammals comprising administering an effective amount of a compound of formula I. The term "effective amount", as defined herein, means the amount of compound necessary to provide a hypoglycemic effect following administration, preferably to a mammal susceptible to adult onset diabetes.

The hypoglycemic activity of the compounds of the present invention was determined by testing the efficacy of the compounds in vivo in viable yellow obese-diabetic mice. The test procedure is described in detail below.

Test formulations were prepared by dissolving the test compound in a saline solution containing 2% Emulphor (a polyoxyethylated vegetable oil surfactant from GAF Corp.) to provide a dose level of 100 mg/kg. Each test formulation was administered to six viable yellow obese-diabetic mice by gavage at 0, 24 and 48 hours. Evaluations of blood glucose levels were recorded immediately before the first dose and at 51 hours. Blood glucose levels were determined by measuring glucose oxidase. A mean was taken of the 6 values, calculated as a percentage of control, and the data is reported in Table 1, below. In Table 1, Column 1 provides the Example Number of the test compound and Column 2 provides a measurement of the test compound's ability to lower blood glucose levels.

TABLE 1

| Hypoglycemic Activity of Test Compounds | |
|---|---|
| Example Number of Compound Tested | Percent of Pre-treatment Glucose Level |
| 1 | 74 |
| 2 | 82 |
| 3 | 78 |
| 4 | 67 |
| 5 | 89 |
| 6 | 72 |
| 7 | 71 |
| 8 | 91 |
| 9 | 66 |
| 10 | 69 |
| 11 | 69 |
| 12 | 61 |
| 13 | 39 |
| 14 | 83 |
| 15 | 61 |
| 16 | 64 |
| 17 | 49 |
| 18 | 70 |
| 19 | 71 |
| 20 | 75 |
| 21 | 75 |
| 22 | 82 |
| 23 | 81 |
| 24 | 82 |
| 25 | 62 |
| 26 | 70 |
| 27 | 81 |
| 28 | 65 |
| 29 | 60 |
| 30 | 79 |
| 31 | 48 |
| 32 | 82 |
| 33 | 78 |
| 34 | 75 |
| 35 | 79 |
| 36 | 69 |
| 37 | 73 |
| 38 | 79 |
| 39 | 72 |
| 40 | 68 |
| 41 | 75 |
| 42 | 80 |
| 43 | 51 |
| 44 | 56 |
| 45 | 55 |
| 47 | 49 |

In addition to the compounds whose hypoglycemic activity is disclosed in Table 1, N-[3-(4-morpholinyl)-propyl]-2-[[4-chlorobenzoyl]amino]benzamide was also tested in the test system set forth above. The morpholinyl compound lowered the test animals' blood glucose levels 78% as compared to pre-treatment glucose levels.

One advantage possessed by the compounds of the present invention is that in addition to being able to lower blood glucose levels in mammals, the present compounds also, in general, exhibit lower toxicity in the ethylmorphine N-demethylation toxicity test system than previously known hypoglycemic agents. Such test system is described in *Biochem. Pharm.*, 36(10), 1669–1672 (1987). The results obtained when the present compounds were tested in the ethylmorphine N-demethylation test system are reported in Table 2, below. In Table 2, Column 1 provides the Example Number of the test compound and Column 2 provides a measurement of the test compound's toxicity at a dosage level of 50 μM as compared to that of a non-toxic control (solvent alone). The test is also performed on a positive control group (2,4 dichloro-6-phenylphenoxyethylamine) as well.

TABLE 2

Toxicity of Test Compounds

| Example Number of Compound Tested | Percent of Control |
|---|---|
| 1 | 5 |
| 3 | 42 |
| 4 | 60 |
| 5 | 60 |
| 6 | 52 |
| 7 | 77 |
| 8 | 33 |
| 9 | 59 |
| 10 | 10 |
| 11 | 36 |
| 12 | 41 |
| 13 | 92 |
| 14 | 94 |
| 15 | 68 |
| 16 | 43 |
| 17 | 96 |
| 20 | 89 |
| 21 | 85 |
| 22 | 91 |
| 23 | 20 |
| 25 | 22 |
| 26 | 5 |
| 27 | 31 |
| 28 | 0 |
| 29 | 0 |
| 30 | 93 |
| 31 | 74 |
| 32 | 90 |
| 33 | 81 |
| 34 | 90 |
| 35 | 11 |
| 36 | 51 |

The active compounds are effective over a wide dosage range. For example, dosages per day will normally fall within the range of about 0.5 to about 500 mg/kg of body weight. In the treatment of adult humans, the range of about 1.0 to about 100 mg/kg, in single or divided doses, is preferred. However, it will be understood that the amount of the compound actually administered will be determined by a physician in light of the relevant circumstances including the condition to be treated, the choice of compound to be administered, the age, weight, and response of the individual patient, the severity of the patient's symptoms and the chosen route of administration. Therefore, the above dosage ranges are not intended to limit the scope of the invention in any way. While the present compounds are preferable administered orally to reduce blood glucose levels in mammals, the compounds may also be administered by a variety of other routes such as the transdermal, subcutaneous, intranasal, intramuscular and intravenous routes.

While it is possible to administer a compound of the invention directly without any formulation, the compounds are preferably employed in the form of a pharmaceutical formulation comprising a pharmaceutically acceptable carrier, diluent or excipient and a compound of the invention. Such formulations will contain from about 0.1 percent to about 90 percent of a compound of the invention.

In making the formulations of the present invention, the active ingredient will usually be mixed with at least one carrier, or diluted by at least one carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the formulations can be in the form of tablets, granules, pills, powders, lozenges, sachets, cachets, elixirs, emulsions, solutions, syrups, suspensions, aerosols (as a solid or in a liquid medium) and soft and hard gelatin capsules.

Examples of suitable carriers, diluents and excipients include lactose, dextrose, sucrose, sorbitol, mannitol, starches, gum acacia, calcium phosphate, alginates, liquid paraffin, calcium silicate, microcrystalline cellulose, polyvinyl pyrrolidone, cellulose, tragacanth gelatin, syrup, methyl cellulose, methyl- and propyl-hydroxybenzoates, vegetable oils, such as olive oil, injectable organic esters such as ethyl oleate, talc, magnesium stearate, water and mineral oil. The formulations may also include wetting agents, lubricating, emulsifying and suspending agents, preserving agents, sweetening agents, perfuming agents, stabilizing agents or flavoring agents. The formulations of the invention may be formulated so as to provide quick, sustained or delayed release of the active ingredient after administration to the patient by employing procedures well-known in the art.

For oral administration, a compound of this invention ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier, diluent or excipient therefor.

In order to more fully illustrate the operation of this invention, the following examples of formulations are provided. The examples are illustrative only and are not intended to limit the scope of the invention. The formulations may employ as active compounds any of the compounds of the present invention.

FORMULATION 1

Hard gelatin capsules are prepared using the following ingredients:

| | Amt. per Capsule | Concentration by Weight (percent) |
|---|---|---|
| Compound of Example No. 15 | 250 mg | 55.0 |
| Starch dried | 200 mg | 43.0 |
| Magnesium stearate | 10 mg | 2.0 |
| | 460 mg | 100.0 |

The above ingredients are mixed and filled into hard gelatin capsules in 460 mg quantities.

FORMULATION 2

Capsules each containing 20 mg of medicament are made as follows:

| | Amt. per Capsule | Concentration by Weight (percent) |
|---|---|---|
| Compound of Example No. 11 | 20 mg | 10.0 |
| Starch | 89 mg | 44.5 |
| Microcrystalline cellulose | 89 mg | 44.5 |
| Magnesium stearate | 2 mg | 1.0 |

-continued

|  | Amt. per Capsule | Concentration by Weight (percent) |
|---|---|---|
|  | 200 mg | 100.0 |

The active ingredient, cellulose, starch and magnesium stearate are blended, passed through a No. 45 mesh U.S. sieve and filled into a hard gelatin capsule.

FORMULATION 3

Capsules each containing 100 mg of active ingredient are made as follows:

|  | Amt. per Capsule | Concentration by Weight (percent) |
|---|---|---|
| Compound of Example No. 9 | 100 mg | 29.0 |
| Polyoxyethylenesorbitan monooleate | 50 mcg | 0.02 |
| Starch powder | 250 mg | 71.0 |
|  | 350.05 mg | 100.02 |

The above ingredients are thoroughly mixed and placed in an empty gelatin capsule.

FORMULATION 4

Tablets each containing 10 mg of active ingredient are made up as follows:

|  | Amt. per Capsule | Concentration by Weight (percent) |
|---|---|---|
| Compound of Example No. 4 | 10 mg | 10.0 |
| Starch | 45 mg | 45.0 |
| Microcrystalline cellulose | 35 mg | 35.0 |
| Polyvinyl pyrrolidone (as 10% solution in water) | 4 mg | 4.0 |
| Sodium carboxymethyl starch | 4.5 mg | 4.5 |
| Magnesium stearate | 0.5 mg | 0.5 |
| Talc | 1 mg | 1.0 |
|  | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

FORMULATION 5

A tablet formula may be prepared using the ingredients below:

|  | Amt. per Capsule | Concentration by Weight (percent) |
|---|---|---|
| Compound of Example No. 16 | 250 mg | 38.0 |
| Cellulose microcrystalline | 400 mg | 60.0 |
| Silicon dioxide fumed | 10 mg | 1.5 |
| Stearic acid | 5 mg | 0.5 |

-continued

|  | Amt. per Capsule | Concentration by Weight (percent) |
|---|---|---|
|  | 665 mg | 100.0 |

The components are blended and compressed to form tablets each weighing 665 mg.

FORMULATION 6

Suspensions each containing 5 mg of medicament per 40 ml dose are made as follows:

|  | per 5 ml of suspension |
|---|---|
| Compound of Example No. 36 | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

FORMULATION 7

An aerosol solution is prepared containing the following components:

|  | Concentration by Weight (%) |
|---|---|
| Compound of Example No. 40 | 0.25 |
| Ethanol | 29.75 |
| Propellant 22 (Chlorodifluoromethane) | 70.00 |
|  | 100.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. A compound of the formula $$\begin{array}{c} \phantom{xxxxxxxx}(R^3)_n \\ \phantom{xxxxx} Z \phantom{xx} Z \\ R^1 \phantom{xxx} R^2 \\ R^0-A^0-N-A^1 \phantom{xx} N \\ \phantom{xxxxxxxxxx} A^2-B^1 \end{array}$$

wherein:

$R^0$ is

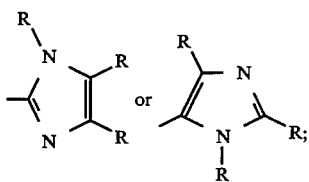

each R is hydrogen or methyl;
$A^0$ is methylene, ethylene or n-propylene;
$R^1$ is hydrogen or methyl;
$A^1$ is a carbonyl or sulfonyl moiety;
Z is —CH—;
$R^3$ $C_1$-$C_4$ alkyl, halo, hydroxy, amino, trifluoromethyl, $C_1$-$C_4$ alkylamino, $C_1$-$C_4$ dialkylamino, nitro, cyano, carboxy, $C_1$-$C_4$ alkoxycarbonyl or $C_1$-$C_4$ alkoxy;
n is 0, 1, 2 or 3;
$R^2$ is hydrogen or methyl;
$A^2$ is a carbonyl or sulfonyl moiety;
$B^1$ is

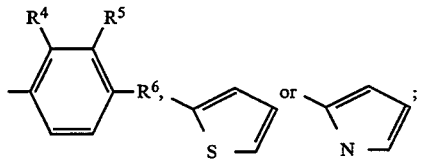

$R^4$ is hydrogen or halo;
$R^5$ is hydrogen, 1,1-dimethylethyl or trifluoromethyl;
$R^6$ is hydrogen, halo or $C_1$-$C_6$ alkyl; with the provisos that:
i. at least one of $R^4$, $R^5$ and $R^6$ must be other than hydrogen;
ii. when $R^5$ is trifluoromethyl, $R^4$ and $R^6$ are hydrogen and $R^0$ is

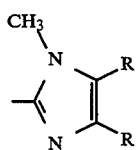

then $A^2$ must be a sulfonyl moiety;
iii. when $R^5$ is trifluoromethyl, $R^4$ and $R^6$ are hydrogen and $R^0$ is

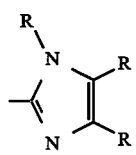

then $A^1$ must be a carbonyl moiety;
iv. when $R^6$ is fluoro, bromo or iodo, $R^4$ and $R^5$ are hydrogen and $R^0$ is

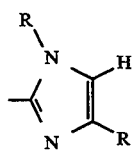

then $A^2$ must be a carbonyl moiety;
v. $R^6$ is chloro, $R^4$ and $R^5$ are hydrogen and $R^0$ is

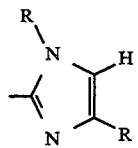

then $A^2$ must be a carbonyl moietyl and $A^1$ must be a sulfonyl moiety;
vi. when $R^4$ and $R^5$ are hydrogen and $R^0$ is

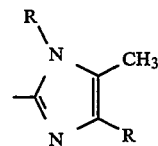

then $R^6$ must be other than chloro;
vii. when $R^6$ is halo, $R^4$ and $R^5$ are hydrogen and $R^0$ is

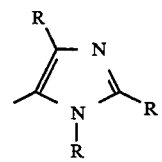

then at least one of $A^1$ or $A^2$ must be a sulfonyl moiety;
viii. when $B^1$ is

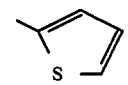

then at least one of $A^1$ or $A^2$ must be a sulfonyl moiety; or a pharmaceutically acceptable salt thereof.

2. The compound of claim 1 which is N-[2-[[[2-(1H-imidazol-2-yl)ethyl]amino]sulfonyl]phenyl]-4-chlorobenzamide or a pharmaceutically acceptable salt thereof.

3. The compound of claim 1 which is N-[2-(1H-imidazol-2-yl)ethyl]-2-[[4-(1,1-dimethylethyl)benzoyl]-amino]benzamide or a pharmaceutically acceptable salt thereof.

4. The compound of claim 1 which is N-[2-(1H-imidazol-2-yl)ethyl]-2-[[4-(1-methylethyl)benzoyl]-amino]benzamide or a pharmaceutically acceptable salt thereof.

5. The compound of claim 1 which is N-[2-(1H-imidazol-2-yl)ethyl]-2-[[3-(trifluoromethyl)benzoyl]-amino]benzamide or a pharmaceutically acceptable salt thereof.

6. The compound of claim 1 which is N-[2-(1H-imidazol-2-yl)ethyl]-2-[[[3-(trifluoromethyl)phenyl]-sulfonyl]amino]benzamide or a pharmaceutically acceptable salt thereof.

7. The compound of claim 1 which is N-[3-(1H-imidazol-2-yl)propyl]-2-[[4-(1,1-dimethylethyl)benzoyl]-amino]benzamide or a pharmaceutically acceptable salt thereof.

8. The compound of claim 1 which is N'-methyl-N-[2-(1H-imidazol-2-yl)ethyl]-2-[[3-(trifluoromethyl)benzoyl]amino]benzamide or a pharmaceutically acceptable salt thereof.

9. A pharmaceutical formulation comprising as an active ingredient, a therapeutically effective amount of a compound of claim 1, or a pharmaceutically acceptable salt thereof, combined with one or more pharmaceutically acceptable carriers, diluents or excipients therefor.

10. A formulation of claim 9 wherein the active ingredient is N-[2-[[[2-(1H-imidazol-2-yl)ethyl]amino]-sulfonyl]phenyl]-4-chlorobenzamide or a pharmaceutically acceptable salt thereof.

11. A formulation of claim 9 wherein the active ingredient is N-[2-(1H-imidazol-2-yl)ethyl]-2-[[4-(1,1-dimethylethyl)benzoyl]amino]benzamide or a pharmaceutically acceptable salt thereof.

12. A formulation of claim 9 wherein the active ingredient is N-[2-(1H-imidazol-2-yl)ethyl]-2-[[4-(1methylethyl)benzoyl]amino]benzamide or a pharmaceutically acceptable salt thereof.

13. A formulation of claim 9 wherein the active ingredient is N-[2-(1H-imidazol-2-yl)ethyl]-2-[[3-(trifluoromethyl)benzoyl]amino]benzamide or a pharmaceutically acceptable salt thereof.

14. A formulation of claim 9 wherein the active ingredient is N-[2-(1H-imidazol-2-yl)ethyl]-2-[[[3-(trifluoromethyl)phenyl]sulfonyl]amino]benzamide or a pharmaceutically acceptable salt thereof.

15. A formulation of claim 9 wherein the active ingredient is N-[3-(1H-imidazol-2-yl)propyl]-2-[[4-(1,1dimethylethyl)benzoyl]amino]benzamide or a pharmaceutically acceptable salt thereof.

16. A formulation of claim 9 wherein the active ingredient is N'-methyl-N-[2-(1H-imidazol-2-yl)ethyl]-2-[[3-(trifluoromethyl)benzoyl]amino]benzamide or a pharmaceutically acceptable salt thereof.

17. A method for lowering blood glucose levels in a mammal comprising administering an effective amount of a compound of claim 1 or a pharmaceutically acceptable salt thereof, to a mammal in need of having its blood glucose level lowered.

18. The method of claim 17 which employs N-[2-[[[2-(1H-imidazol-2-yl)ethyl]amino]sulfonyl]phenyl]-4-chlorobenzamide or a pharmaceutically acceptable salt thereof.

19. The method of claim 17 which employs N-[2-(1H-imidazol-2-yl)ethyl]-2-[[4-(1,1-dimethylethyl)benzoyl]amino]-benzamide or a pharmaceutically acceptable salt thereof.

20. The method of claim 17 which employs N-[2-(1H-imidazol-2-yl)ethyl]-2-[[4-(1-methylethyl)benzoyl]amino]-benzamide or a pharmaceutically acceptable salt thereof.

21. The method of claim 17 which employs N-[2-(1H-imidazol-2-yl)ethyl]-2-[[3-(trifluoromethyl)benzoyl]amino]-benzamide or a pharmaceutically acceptable salt thereof.

22. The method of claim 17 which employs N-[2-(1H-imidazol-2-yl)ethyl]-2-[[[3-(trifluoromethyl)phenyl]-sulfonyl]amino]benzamide or a pharmaceutically acceptable salt thereof.

23. The method of claim 17 which employs N-[3-(1H-imidazol-2-yl)propyl]-2-[[4-(1,1-dimethylethyl)benzoyl]-amino]benzamide or a pharmaceutically acceptable salt thereof.

24. The method of claim 17 which employs N'-methyl-N-[2(1H-imidazol-2-yl)ethyl]-2-[[3-(trifluoromethyl)-benzoyl]-amino]benzamide or a pharmaceutically acceptable salt thereof.

* * * * *

UNITED STATES PATENT AND TRADEMARK OFFICE
CERTIFICATE OF CORRECTION

PATENT NO. : 5,397,798

DATED : March 14, 1995

INVENTOR(S) : Lora L. Fitch et al.

It is certified that an error appears in the above-identified patent and that said Letters Patent is hereby corrected as shown below:

Column 14, line 6, "amino compounds" should read -- amino substituted compounds --.

Column 16, line 25, "ethanol/water water" should read -- ethanol/water --.

Column 22, line 47, "$C_{10}H_{12}N_60$" should read -- $C_{10}H_{12}N_6O$ --.

Column 22, line 49, "Be" should read -- B. --

Column 27, line 11, "fluoromethylbenzoyl-benzoyl" should read -- fluoromethylbenzoyl --.

Signed and Sealed this

Third Day of October, 1995

Attest:

BRUCE LEHMAN

*Attesting Officer*     *Commissioner of Patents and Trademarks*